United States Patent
Paulse et al.

(10) Patent No.: US 7,027,933 B2
(45) Date of Patent: Apr. 11, 2006

(54) METHOD FOR ANALYZING MASS SPECTRA

(75) Inventors: Chris D. Paulse, Palo Alto, CA (US); Edward J. Gavin, San Jose, CA (US); Leonid Braginsky, Newton, MA (US); William E. Rich, Redwood Shores, CA (US); Eric T. Fung, Cupertino, CA (US)

(73) Assignee: Ciphergen Biosystems, Inc., Fremont, CA (US)

( * ) Notice: Subject to any disclaimer, the term of this patent is extended or adjusted under 35 U.S.C. 154(b) by 0 days.

(21) Appl. No.: 10/669,499

(22) Filed: Sep. 23, 2003

(65) Prior Publication Data

US 2004/0059530 A1   Mar. 25, 2004

Related U.S. Application Data

(63) Continuation of application No. 09/999,081, filed on Nov. 15, 2001, now Pat. No. 6,675,104.

(60) Provisional application No. 60/254,746, filed on Dec. 11, 2000, provisional application No. 60/249,835, filed on Nov. 16, 2000.

(51) Int. Cl.
    *G01R 23/16* (2006.01)

(52) U.S. Cl. .................................................. 702/27

(58) Field of Classification Search .............. 702/27, 702/76, 28, 22, 30, 23; 250/282, 288, 291, 250/292, 360; 713/193; 707/1; 422/70; 436/518; 435/7.1, 4

See application file for complete search history.

(56) References Cited

U.S. PATENT DOCUMENTS

| | | | |
|---|---|---|---|
| 4,122,343 A | 10/1978 | Risby et al. | |
| 5,136,686 A | 8/1992 | Koza | |
| 5,687,716 A | 11/1997 | Kaufmann et al. | |
| 5,697,369 A | 12/1997 | Long, Jr. et al. | |
| 5,716,825 A | 2/1998 | Hancock et al. | |
| 5,790,761 A | 8/1998 | Heseltine et al. | |
| 5,839,438 A | 11/1998 | Graettinger et al. | |
| 5,905,258 A | 5/1999 | Clemmer et al. | |
| 5,946,640 A | 8/1999 | Goodacre et al. | |
| 6,025,128 A | 2/2000 | Veltri et al. | |
| 6,128,608 A | 10/2000 | Barnhill | |
| 6,157,921 A | 12/2000 | Barnhill | |

(Continued)

FOREIGN PATENT DOCUMENTS

WO   WO 01/20043 A1   3/2001

(Continued)

OTHER PUBLICATIONS

Alaiya et al., "Classification of Human Ovarian Tumors Using Multivariate Data Analysis of Polypeptide Expression Patterns," Int. J. Cancer, vol. 86, pp. 731-736, Wiley-Liss, Inc., (2000).

(Continued)

*Primary Examiner*—John Barlow
*Assistant Examiner*—Tung Lau
(74) *Attorney, Agent, or Firm*—Townsend and Townsend and Crew LLP

(57) ABSTRACT

A method that analyzes mass spectra using a digital computer is disclosed. The method includes entering into a digital computer a data set obtained from mass spectra from a plurality of samples. Each sample is, or is to be assigned to a class within a class set having two or more classes and each class is characterized by a different biological status. A classification model is then formed. The classification model discriminates between the classes in the class set.

12 Claims, 10 Drawing Sheets

U.S. PATENT DOCUMENTS

| | | | |
|---|---|---|---|
| 6,289,287 B1* | 9/2001 | Meng et al. | 702/23 |
| 6,329,652 B1 | 12/2001 | Windig et al. | |
| 6,427,141 B1 | 7/2002 | Barnhill | |
| 6,558,902 B1 | 5/2003 | Hillenkamp | |
| 6,647,343 B1* | 11/2003 | Guthrie et al. | 702/30 |
| 2001/0021535 A1* | 9/2001 | Nelson et al. | 436/518 |
| 2001/0033809 A1* | 10/2001 | Karger et al. | 422/70 |
| 2002/0023078 A1* | 2/2002 | Liebler et al. | 707/1 |
| 2002/0046198 A1 | 4/2002 | Hitt | |
| 2002/0138208 A1 | 9/2002 | Paulse et al. | |
| 2002/0193950 A1 | 12/2002 | Gavin et al. | |
| 2003/0004402 A1 | 1/2003 | Hitt et al. | |
| 2003/0034450 A1* | 2/2003 | Karger et al. | 250/288 |

FOREIGN PATENT DOCUMENTS

| | | | |
|---|---|---|---|
| WO | WO 01/31579 A2 | 5/2001 | |
| WO | WO 01/31580 A2 | 5/2001 | |
| WO | WO 01/84140 A2 | 11/2001 | |
| WO | WO 01/99043 A1 | 12/2001 | |
| WO | WO 02/06829 A2 | 1/2002 | |
| WO | WO 02/059822 A2 | 8/2002 | |
| WO | WO 02/088744 A2 | 11/2002 | |

OTHER PUBLICATIONS

Ashfaq, et al., "Evaluation of PAPNET.TM. System for Rescreening of Negative Cervical Smears", Diagnostic Cytopathology, 1995, pp. 31-36, vol. 13, No. 1.

Astion, et al., The Application of Backpropagation Neural Networks to Problems in Pathology and Laboratory Medicine, Arch Pathol Lab Med, Oct. 1992, pp. 995-1001, vol. 116.

Atkinson, Ph.D., et al., "Statistical Techniques for Diagnosing CIN Using Fluorescence Spectroscopy: SVD and CART", Journal of Cellular Biochemistry, Supplement, 1995, pp. 125-130, vol. 23.

Babaian, et al., "Performance of a Neural Network in Detecting Prostate Cancer in the Prostate-Specific Antigen Reflex Range of 2.5 to 4.0 ng/mL", Urology, 2000, pp. 1000-1006, vol. 56, No. 6.

Bailey-Kellogg et al., "Reducing Mass Degeneracy in SAR by MSby Stable Isotopic Labeling." Journal of Computational Biology, vol. 8, No. 1, pp 19-36, Mary Ann Liebert, Inc., (2001).

Belic, "Neural Networks Methodologies for Mass Spectra Recognition", 4 pgs.

Belic, et al., "Neural network methodologies for mass spectra recognition", Vacuum, 1997, pp. 633-637, vol. 48, Nos. 7-9.

Berikov, et al., "Regression trees for analysis of mutational spectra in nucleotide sequences", Bioinformatics, 1999, pp. 553-562, vol. 15, Nos. 7/8.

Breiman, et al., Chapters 6-8 in Classification and Regression Trees, CRC Press (Boca Raton), 1998, pp. 174-265.

Cairns, et al., "Towards the Automated Prescreening of Breast X-Rays", Digest of the IEE Colloquium, Applications of Image Processing in Mass Health Screening, University of Dundee, pp. 1/1-1/5.

Caprioli et al. "Molecular Imaging of Biological Samples: Localization of Peptides and Proteins Using MALDI-TOF MS." Analytical Chemistry, vol. 69, No. 23, pp 4751-4760, American Chemical Society, (Dec. 1, 1997).

Chace, et al., "Laboratory integration and utilization of tandem mass spectrometry in neonatal screening: a model for clinical mass spectrometry in the next millennium", Acta Paediatr Supp 432, 1999, pp. 45-47, vol. 88.

Chun, et al., "Long-term Identification of Streptomycetes Using Pyrolysis Mass Spectrometry and Artificial Neural Networks", Zbl. Bakt., 1997, pp. 258-266, vol. 285.

Cicchetti, "Neural Networks and Diagnosis in the Clinical Laboratory: State of the Art", Clin. Chem., 1992, pp. 9-10, vol. 38, No. 1.

Crawford, et al., "Computer Methods in Analytical Mass Spectrometry. Empirical Identification of Molecular Class", Analytical Chemistry, Aug., 1968, pp. 1469-1474, vol. 40, No. 10.

Curry, et al., "MSnet: A Neural Network That Classifies Mass Spectra", Stanford Science Center, Stanford University, Stanford, California, Oct. 1990, pp. 1-31.

Dudoit, et al., "Comparison of Discrimination Methods for the Classification of Tumors Using Gene Expression Data", Technical report #576, Jun. 2000, pp. 1-43.

Dudoit, et al., "Comparison of discrimination methods for the classification of tumors using gene expression data", UC Berkeley, Slides, 52 pages, URL=http://stat-www.berkeley.edu/users/terry/zarray/Html/discr.html, (Mar. 7, 2000).

Dzeroski, et al., "Diterpene Structure Elucidation From .sup.—C NMR-Spectra With Machine Learning", Chapter 12 in Intelligent Data Analysis in Medicine and Pharmacology, N. Lavrac, et al. ed., Kluwer Academic Publishers (Boston), 1997, pp. 207-225.

Eghbaldar, et al., "Identification of Structural Features from Mass Spectrometry Using a Neural Network Approach: Application of Trimethylsilyl Derivatives Used for Medical Diagnosis", J. Chem. Inf. Comput. Sci., 1996, pp. 637-643, vol. 36.

Freeman, et al., "Resolution of batch variations in pyrolysis mass spectrometry of bacteria by the use of artificial neural network analysis", Antonie van Leeuwenhoek, 1995, pp. 253-260, vol. 68.

Furlong, et al., "Neural Network Analysis of Serial Cardiac Enzyme Data, A Clinical Application of Artificial Machine Intelligence", Am J Clin Pathol, 1991, pp. 134-141, vol. 96.

George, "A Visualization and Design Tool (AVID for Data Mining with the Self-Organizing Feature Map." International Journal on Artificial Intelligence Tools, vol. 9, No. 3, pp. 369-375, World Scientific Publishing Company, (2000).

Goodacre, "Rapid identification of urinary tract infection bacteria using hyperspectral whole-organism fingerprinting and artificial neutral networks", Microbiology, 1998, pp. 1157-1170, vol. 144.

Goodacre, et al., "Correction of Mass Spectral Drift Using Artificial Neural Networks", Anal. Chem., 1996, pp. 271-280, vol. 68.

Goodacre, et al., "Identification and Discrimination of Oral Asaccharolytic Eubacterium spp. by Pyrolysis Mass Spectrometry and Artificial Neural Networks", Current Microbiology, 1996, pp. 77-84, vol. 32.

Goodacre, et al., "Quantitative Analysis of Multivariate Data Using Artificial Neural Networks: A Tutorial Review and Applications to the Deconvolution of Pyrolysis Mass Spectra", Zbl. Bakt., 1996, pp. 516-539, vol. 284.

Goodacre, et al., "Sub-species Discrimination, Using Pyrolysis Mass Spectrometry and Self-organising Neural Networks, of Propionibacterium acnes Isolated from Normal Human Skin", Zbl. Bakt., 1996; pp. 501-515, vol. 284.

Goodacre, et al., Discrimination between methicillin-resistant and methicillin-susceptible *Staphylococcus aureus* using pyrolysis mass spectrometry and artificial neutral networks, Journal of Antimicrobial Chemotherapy, 1998, pp. 27-34, vol. 41.

Gray, "Constraints on 'Learning Machine' Classification Methods", Analytical Chemistry, Dec. 1976, pp. 2265-2268, vol. 48, No. 14.

Gustav Schroll, et al., "Applications of Artificial Intelligence for Chemical Inference. III. Aliphatic Ethers Diagnosed by Their Low-Resolution Mass Spectra and Nuclear Magnetic Resonance Data", Journal of the American Chemical Society, Dec. 17, 1969, pp. 7440-7445, vol. 91, No. 26.

Halket, et al., "Deconvolution Gas Chromatography/Mass Spectrometry of Urinary Organic Acids—Potential for Pattern Recognition and Automated Identification of Metabolic Disorders", Rapid Commun. Mass Spectrom, 1999, pp. 279-284, vol. 13.

Hashemi, et al., "Identifying and Testing of Signatures for Non-Volatile Biomolecules Using Tandem Mass Spectra", Sigbio newsletter, ACM Press, Dec. 1995, pp. 11-19, vol. 15, No. 3.

Hausen, et al., "Determination of Neopterine in Human Urine by Reversed-Phase High-Performance Liquid Chromatography", Journal of Chromatography, 1982, pp. 61-70, vol. 227.

Jain, et al., "Statistical Pattern Recognition: A Review", IEEE Transactions on Pattern Analysis and Machine intelligence, Jan. 2000, pp. 4-37, vol. 22, No. 1.

Jellum, et al., "Mass Spectrometry in Diagnosis of Metabolic.Disorders", Biomedical and Environmental Mass Spectrometry, 1988, pp. 57-62, vol. 16.

Jurs, et al., "Computerized Learning Machines Applied to Chemical Problems. Molecular Formula Determination from Low Resolution Mass Spectrometry", Analytical Chemistry, Jan. 1969, pp. 21-27, vol. 41, No. 1.

Kenyon, et al., "Application of Neural Networks to the Analysis of Pyrolysis Mass Spectra", Zbl. Bakt., 1997, pp. 267-277, vol. 285.

Kohavi et al., "Wrappers for Feature Subset Selection." Artificial Intelligence, vol. 97, No. 1-2, pp. 273-324, Elsevier Science B.V., (1997).

Kohno, et al., "Quantitative Analysis of Scintiscan Matrices by Computer", Japanese Journal of Medical Electronics and Biological Engineering, Aug. 1974, pp. 218-225, vol. 12, No. 4.

Lowry, et al., "Comparison of Various K-Nearest Neighbor Voting Schemes with the Self-Training Interpretive and Retrieval System for Identifying Molecular Substructures from Mass Spectral Data", Analytical Chemistry, Oct. 1977, pp. 1720-1722, vol. 49, No. 12.

Macfie, et al., "Use of Canonical Variates Analysis in Differentiation of Bacteria by Pyrolysis Gas-Liquid Chromatography", Journal of General Microbiology, 1978, pp. 67-74, vol. 104.

Malins, et al., "Models of DNA structure achieve almost perfect discrimination between normal prostate, benign prostatic hyperplasia (BPH), and adenocarcinoma and have a high potential for predicting BPH and prostase cancer", Proc. Natl. Acad. Sci. USA, Jan. 1997, pp. 259-264, vol. 94.

Marvin et al., "Characterization of a novel Sepia officinalls neuropeptide using MALDI-TOF MS and post-source decay analysis." Peptides, vol. 22, No. 9., pp 1391-1396, Elsevier Science Inc., (Sep. 2001).

Meuzelaar, et al., "A Technique for Fast and Reproducible Fingerprinting of Bacteria by Pyrolysis Mass Spectrometry", Analytical Chemistry, Mar. 1973, pp. 587-590, vol. 45, No. 3.

Meyer, et al., "Identification of the .sup.1 H-NMR Spectra of Complex Oligosaccharides with Artificial Neural Networks". Science, Feb. 1991, pp. 542-544, vol. 251.

Nikulin, et al., "Near-optimal region selection for feature space reduction: novel preprocessing methods for classifying MR spectra", NMR in Biomedicine, (1998), 209-216, vol. 11.

Nilsson, et al., "Classification of Species in the Genus Penicillium by Curie Point Pyrolysis/Mass Spectrometry Followed by Multivariate Analysis and Artificial Neural Networks", Journal of Mass Spectrometry, 1996, pp. 1422-1428, vol. 31.

Oh et al., "A Database of Protein Expression in Lung Cancer." Proteomics, 1, pp. 1303-1319, WILEY-VCH Verlag GmbH, (2001).

Paweletz, et al., "Rapid Protein Display Profiling of Cancer Progression Directly From Human tissue Using a Protein Biochip", Drug Development Research, 2000pp. 34-42, vol. 49.

Prior, et al., "Potential of Urinary Neopterin Excretion in Differentiating Chronic Non-A, Non-B Hepatitis From Fatty Liver", The Lancet, Nov. 1987, pp. 1235-1237.

Reibnegger, et al., "Neural networks as a tool for utilizing laboratory information: Comparison with linear discriminant analysis and with classification and regression trees", Proc. Natl. Acad. Sci. USA, Dec. 1991. pp. 11426-11430, vol. 88.

Ricketts, et al., "Towards the Automated Prescreening of Cervical Smears", IEE Colloquium on Applications of Image Processing in Mass Health Screening, Digest No. 056, Mar. 11, 1992, pp. 7/1-7/4.

Salford Systems White Paper Series, http://www.salford-systems.com/whitepaper.html, printed Oct. 17, 2000.

Shaw, et al., "Infrared Spectroscopy of Exfoliated Cervical Cell Specimens", Analytical and Quantitative Cytology and Histology, Aug. 1999, pp. 292-302, vol. 21, No. 4.

Shevchenko, et al., "MALDI Quadrupole Time-of-Flight Mass Spectrometry: A Powerful Tool for Proteomic Research", Anal. Chem., 2000, pp. 2132-2141, vol. 72, No. 9.

Strouthopoulos et al., "PLA using RLSA and a Neural Network." Engineering Applications of Artificial Intelligence, vol. 12, No. 2, pp. 119-138, Elsevier Science Ltd., (1999).

Taylor et al., "The Deconvolution of Pyrolysis Mass Spectra using Genetic Programming: Application to the Identification of Some Eubacterium Species." FEMS Microbiology Letters, 160, pp. 237-246, Elsevier Science B.V., (1998).

Taylor, "The deconvolution of pyrolysis mass spectra using genetic programming: application to the identification of some Eubacterium species", FEMS Microbiology Letters, 1998, pp. 237-246, vol. 160.

Tong, et al., "Mass Spectral Search method using the Neural Network approach", Proceedings, International Joint Conference on Neural Networks, Washington, DC, Jul. 1999. pp. 3962-3967, vol. 6.

Tong, et al., "Mass spectral search method using the neural network approach", Chemometrics and Intelligent Laboratory Systems, 1999, pp. 135-150, vol. 49.

Voorhees, et al., "Approaches to Pyrolysis/Mass Spectrometry Data Analysis of Biological Materials", Chapter 11 in Computer-Enhanced Analytical Spectroscopy, H.L.C. Meuzelaar ed., Plenum Press (New York), 1990, pp. 259-275, vol. 2.

Werther, et al., "Classification of mass spectra, A comparison of yes/no classification methods for the recognition of simple structural properties", Chemometrics and Intelligent Laboratory Systems, 1994, pp. 63-76, vol. 22.

Wythoff, et al., "Spectral Peak Verification and Recognition Using a Multilayered Neural Network", Anal, Chem., 1990, pp. 2702-2709, vol. 62.

Yates, III, et. al., "Mass Spectrometry and the Age of the Proteome", Journal of Mass Spectrometry, 1998, pp. 1-19, vol. 33.

Zhang, "Combining Multiple Biomarkers in Clinical Diagnostics—A Review of Methods and Issues." pp. 1-14.

* cited by examiner

VARIABLE IMPORTANCE

| VARIABLE | SCORE | |
|---|---|---|
| P36 | 100.00 | IIIIIIIIIIIIIIIIIIIIIIIIIIIIII |
| P127 | 95.89 | IIIIIIIIIIIIIIIIIIIIIIIIIIIIII |
| P90 | 93.52 | IIIIIIIIIIIIIIIIIIIIIIIIIIIII |
| P185 | 91.57 | IIIIIIIIIIIIIIIIIIIIIIIIIIIII |
| P128 | 76.95 | IIIIIIIIIIIIIIIIIIIIII |
| P119 | 63.80 | IIIIIIIIIIIIIIIIIII |
| P73 | 26.10 | IIIIIIII |
| P21 | 18.18 | IIIIII |
| P193 | 17.93 | IIIIII |
| P50 | 17.30 | IIIIII |
| P94 | 16.84 | IIIII |
| P163 | 13.89 | IIIII |
| P158 | 13.89 | IIIII |
| P190 | 13.89 | IIIII |
| P15 | 13.32 | IIIII |
| P164 | 11.77 | IIII |
| P135 | 11.61 | IIII |
| P16 | 10.01 | III |
| P55 | 9.89 | III |
| P250 | 9.89 | III |
| P54 | 9.89 | III |
| P11 | 9.89 | III |
| P187 | 9.72 | III |
| P209 | 9.69 | III |
| P46 | 6.91 | II |
| P1 | 6.58 | II |
| P78 | 6.58 | II |
| P18 | 3.43 | |
| P6 | 3.43 | |
| P4 | 3.43 | |
| P19 | 0.00 | |
| P2 | 0.00 | |
| P5 | 0.00 | |
| P32 | 0.00 | |
| P3 | 0.00 | |
| P35 | 0.00 | |
| P23 | 0.00 | |

*FIG. 8.*

METHOD FOR ANALYZING MASS SPECTRA

CROSS REFERENCE TO RELATED APPLICATIONS

This application is a continuation application of U.S. patent application Ser. No. 09/999,081, filed Nov. 15, 2001 now U.S. Pat. No. 6,675,104, which claims the benefit of U.S. Provisional Patent Application Nos. 60/249,835 filed Nov. 16, 2000 and 60/254,746 filed Dec. 11, 2000. All of the above provisional and non-provisional patent applications are herein incorporated by reference in their entirety for all purposes.

FIELD OF THE INVENTION

Embodiments of the invention relate to methods for analyzing mass spectra.

BACKGROUND OF THE INVENTION

Recent advances in genomics research have led to the identification of numerous genes associated with various diseases. However, while genomics research can identify genes associated with a genetic predisposition to disease, there is still a need to characterize and identify markers such as proteins. A "marker" typically refers to a polypeptide or some other molecule that differentiates one biological status from another. Proteins and other markers are important factors in disease states. For example, proteins can vary in association with changes in biological states such as disease. They can also signal cellular responses to disease, toxicity, or other stimuli. When disease strikes, some proteins become dormant, while others become active. Prostate Specific Antigen (PSA), for example, is a circulating serum protein that, when elevated, correlates with prostate cancer. If the changes in protein levels could be rapidly detected, physicians could diagnose diseases early and improve treatments.

Identifying novel markers is one of the earliest and most difficult steps in the diagnostics and drug discovery processes. One way to discover if substances are markers for a disease is by determining if they are "differentially expressed" in biological samples from patients exhibiting the disease as compared to samples from patients not having the disease. For example, FIG. 1(a) shows one graph 100 of a plurality of overlaid mass spectra of samples from a group of 18 diseased patients. The diseased patients could have, for example, prostate cancer. Another graph 102 is shown in FIG. 1(b) and illustrates a plurality of overlaid mass spectra of samples from a group of 18 normal patients. In each of the graphs 100, 102, signal intensity is plotted as a function of mass-to-charge ratio. The intensities of the signals shown in the graphs 100, 102 are proportional to the concentrations of markers having a molecular weight related to the mass-to-charge ratio A in the samples. As shown in the graphs 100, 102, at the mass-to-charge ratio A, a number of signals are present in both pluralities of mass spectra. The signals include peaks that represent potential markers having molecular weights related to the mass-to-charge ratio A.

When the signals in the graphs 100, 102 are viewed collectively, it is apparent that the average intensity of the signals at the mass-to-charge ratio A is higher in the samples from diseased patients than the samples from the normal patients. The marker at the mass-to-charge ratio A is said to be "differentially expressed" in diseased patients, because the concentration of this marker is, on average, greater in samples from diseased patients than in samples from normal patients.

In view of the data shown in FIGS. 1(a) and 1(b), it can be generally concluded that the samples from diseased patients have a greater concentration of the marker with the mass-to-charge ratio A than the samples from normal patients. Since the concentration of the marker is generally greater in samples from diseased patients than in the normal samples, the marker can also be characterized as being "up-regulated" for the disease. If the concentration of the marker was generally less in the samples from diseased patients than in the samples from normal patients, the protein could be characterized as being "down-regulated".

Once markers are discovered, they can be used as diagnostic tools. For example, with reference to the example described above, an unknown sample from a test patient may be analyzed using a mass spectrometer and a mass spectrum can be generated. The mass spectrum can be analyzed and the intensity of a signal at the mass-to-charge ratio A can be determined in the test patient's mass spectrum. The signal intensity can be compared to the average signal intensities at the mass-to-charge ratio A for diseased patients and normal patients. A prediction can then be made as to whether the unknown sample indicates that the test patient has or will develop cancer. For example, if the signal intensity at the mass-to-charge ratio A in the unknown sample is much closer to the average signal intensity at the mass-to-charge ratio A for the diseased patient spectra than for the normal patient spectra, then a prediction can be made that the test patient is more likely than not to develop or have the disease.

While the described differential expression analysis is useful, many improvements could be made. For instance, analyzing the amount of a single marker such as PSA in a patient's biological sample is many times not sufficiently reliable to monitor disease processes. PSA is considered to be one of the best prostate cancer markers presently available. However, it does not always correctly differentiate benign from malignant prostate disease. While the concentration of a marker such as PSA in a biological sample provides some ability to predict whether a test patient has a disease, an analytical method with a greater degree of reliability is desirable.

Also, when a large number of mass spectra of a large number of biological samples are analyzed, it is not readily apparent which signals represent markers that might differentiate between a diseased state and a non-diseased state. A typical mass spectrum of a biological sample has numerous potential marker signals (e.g., greater than 200) and a significant amount of noise. This can make the identification of potentially significant signals and the identification of average signal differentials difficult. Consequently, it is difficult to identify and quantify potential markers. Unless the potential markers exhibit strong up-regulation or strong down-regulation, the average signal differential between samples from diseased patients and samples from normal patients may not be easily discernable. For example, it is often difficult to visually determine that a cluster of signals at a given mass value in one group of mass spectra has higher or lower average signal intensity than a cluster of signals from another group of mass spectra. In addition, many potentially significant signals may have low intensity values. The noise in the spectra may obscure many of these potentially significant signals. The signals may go undiscovered and may be inadvertently omitted from a differential expression analysis.

It would be desirable to have better ways to analyze mass spectra. For example, it would be desirable to provide for a more accurate method for discovering potentially useful markers. It would also be desirable to provide an improved classification model that can be used to predict whether an unknown sample is associated or is not associated with a particular biological status.

Embodiments of the invention address these and other problems.

SUMMARY OF THE INVENTION

Embodiments of the invention relate to methods for analyzing mass spectra. In embodiments of the invention, a digital computer forms a classification model that can be used to differentiate classes of samples associated with different biological statuses. The classification model can be used as a diagnostic tool for prediction. It may also be used to identify potential markers associated with a biological status. In addition, the classification model can be formed using a process such as, for example, a recursive partitioning process.

One embodiment of the invention is directed to a method that analyzes mass spectra using a digital computer. The method comprises: entering into a digital computer a data set obtained from mass spectra from a plurality of samples, wherein each sample is, or is to be assigned to a class within a class set comprising two or more classes, each class characterized by a different biological status, and wherein each mass spectrum comprises data representing signal strength as a function of mass-to-charge ratio or a value derived from mass-to-charge ratio; and b) forming a classification model which discriminates between the classes in the class set, wherein forming comprises analyzing the data set by executing code that embodies a classification process comprising a recursive partitioning process.

Another embodiment of the invention is directed to a method that analyzes mass spectra using a digital computer. The method comprises: a) entering into a digital computer a data set obtained from mass spectra from a plurality of samples, wherein each sample is, or is to be assigned to a class within a class set comprising two or more classes, each class characterized by a different biological status, and wherein each mass spectrum comprises data representing signal strength as a function of time-of-flight or a value derived from time-of-flight; and b) forming a classification model which discriminates between the classes in the class set, wherein forming comprises analyzing the data set by executing code that embodies a recursive partitioning process.

Another embodiment is directed to a computer readable medium. The computer readable medium comprises: a) code for entering data derived from mass spectra from a plurality of samples, wherein each sample is, or is to be assigned to a class within a class set of two or more classes, each class characterized by a different biological status, and wherein each mass spectrum comprises data representing signal strength as a function of time-of-flight or a value derived from time-of-flight, or mass-to-charge ratio or a value derived from mass-to-charge ratio; and b) code for forming a classification model using a recursive partitioning process, wherein the classification model discriminates between the classes in the class set. The mass spectra may be created using, for example, a laser desorption ionization process.

Another embodiment of the invention is directed to a method for classifying an unknown sample into a class characterized by a biological status using a digital computer. The method comprises: a) entering data obtained from a mass spectrum of the unknown sample into a digital computer; and b) processing the mass spectrum data using a classification model to classify the unknown sample in a class characterized by a biological status. The classification model may be formed using a recursive partitioning process.

Another embodiment of the invention is directed to a method for estimating the likelihood that an unknown sample is accurately classified as belonging to a class characterized by a biological status using a digital computer. The method comprises: a) entering data obtained from a mass spectrum of the unknown sample into a digital computer; and b) processing the mass spectrum data using a classification model to estimate the likelihood that the unknown sample is accurately classified into a class characterized by a biological status. The classification model may be formed using a recursive partitioning process, and is formed using a data set obtained from mass spectra of samples assigned to two or more classes with different biological statuses.

In embodiments of the invention, the mass spectra being analyzed may be pre-existing mass spectra which, for example, may have been created well before the classification model is formed. Alternatively, the mass spectra data may have been created substantially contemporaneously with the formation of the classification model.

These and other embodiments of the invention are described with reference to the Figures and the Detailed Description.

BRIEF DESCRIPTION OF THE DRAWINGS

FIG. 8 shows a table showing the variable importance of different predictor variables.

DETAILED DESCRIPTION

Figure 1:
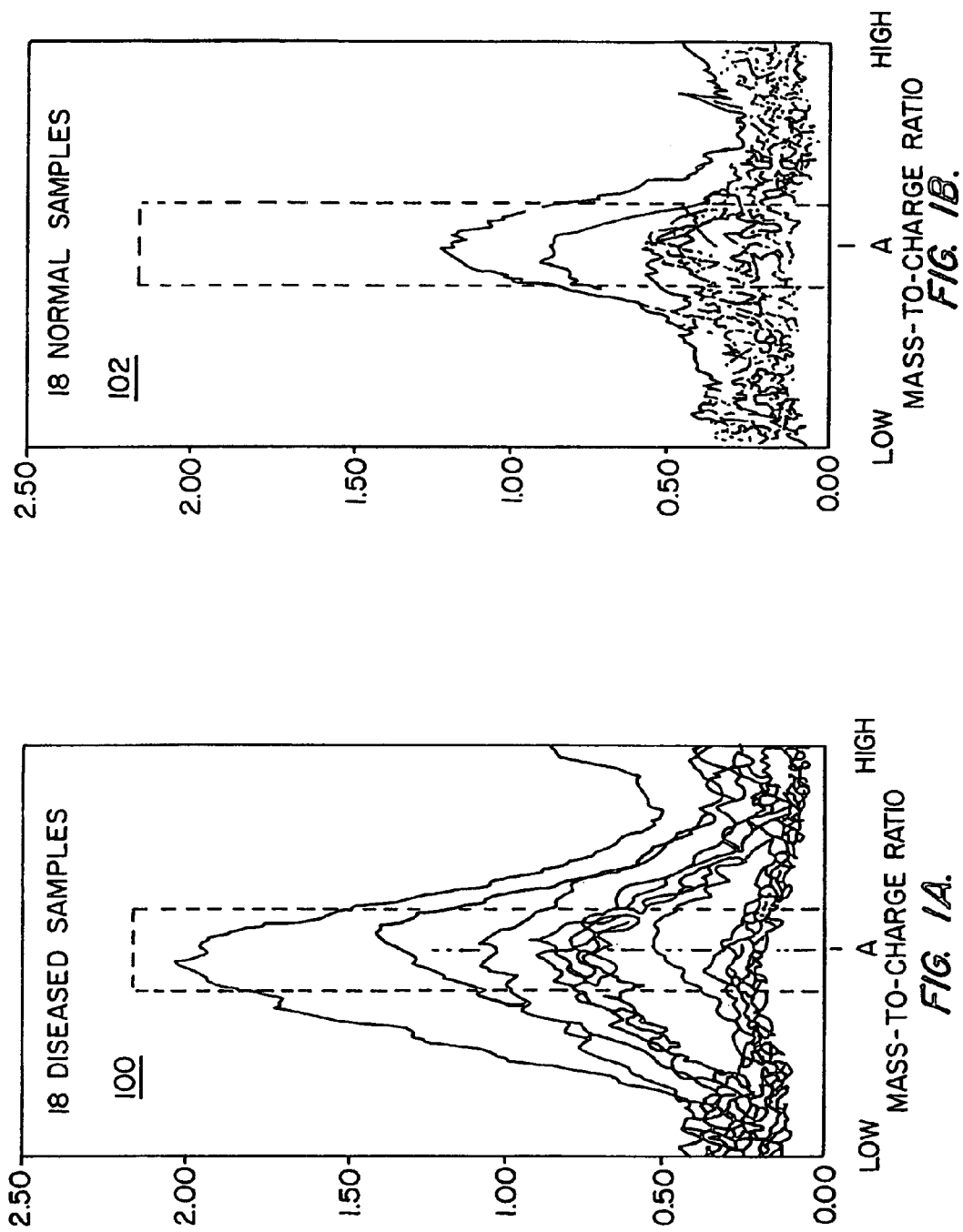
FIG. 1(A) shows overlaid mass spectra for samples from diseased patients.
FIG. 1(B) shows overlaid mass spectra for samples from normal patients.

In embodiments of the invention, a data set obtained from mass spectra is entered into a digital computer to form a classification model. The mass spectra are preferably obtained from biological samples having known characteristics. In preferred embodiments, the data set used to form the classification model is characterized as a "known" data set, because the biological statuses associated with the biological samples are known before the data set is used to form the classification model. In comparison, an "unknown" data set includes data that is obtained from mass spectra of samples where it is unclear if the samples are associated with the biological statuses which are discriminated by the classification model when the mass spectra are formed. Unknown data may be derived from a biological sample from a test patient who is to be diagnosed using the classification model. In some environments, the known data set is referred to as "training data".

For purposes of illustration, many of the examples described below refer to using a known data set to form a classification model. However, in some embodiments of the invention, the data set used to form the classification model may be an unknown data set. For example, in a cluster analysis, mass spectra of unknown biological samples may be grouped together if they have similar patterns. Samples corresponding to each group may be analyzed to see if they have a biological status in common. If so, then the samples in the group may be assigned to a class associated with the biological status. For example, after forming a group of mass spectra having common patterns, it may be determined that all spectra in the group were obtained from biological samples that were all exposed to radiation. The samples in the group may then be assigned to a class that is associated with the status "radiation exposed". Samples in other groupings can be assigned to classes characterized by other biological statuses common to the samples in the respective groupings. A classification model can thus be formed and unknown spectra may be classified using the formed classification model.

In embodiments of the invention, each sample used is, or is to be assigned to a class of a set of two or more classes, and each class is characterized by a different biological status. For example, a first class of samples may be associated with a biological status such as a diseased state. A second class of mass spectra of samples may be associated with a biological status such as a non-diseased state. The samples in the first and second classes may form the class set. The mass spectra from each of the respective classes can contain data that differentiates the first and the second classes.

In embodiments of the invention, each mass spectrum in the analyzed mass spectra could comprise signal strength data as a function of time-of-flight, a value derived from time-of-flight (e.g. mass-to-charge ratio, molecular weight, etc.), mass-to-charge ratio, or a value derived from mass-to-charge ratio (e.g., molecular weight). As known by those of ordinary skill in the art, mass-to-charge ratio values obtained from a time-of-flight mass spectrometer are derived from time-of-flight values. Mass-to-charge ratios may be obtained in other ways. For example, instead of using a time-of-flight mass spectrometer to determine mass-to-charge ratios, mass spectrometers using quadrupole analyzers and magnetic mass analyzers can be used to determine mass-to-charge ratios.

In preferred embodiments, each mass spectrum comprises signal strength data as a function of mass-to-charge ratio. In a typical spectral view-type mass spectrum, the signal strength data may be in the form of "peaks" on a graph of signal intensity as a function of mass-to-charge ratio. Each peak may have a base and an apex, where peak width narrows from the base to the apex. The mass-to-charge ratio generally associated with the peak corresponds to the apex of the peak. The intensity of the peak is also generally associated with the apex of the peak.

Generally, the mass-to-charge ratio relates to the molecular weight of a potential marker. For example, if a potential marker has a charge of +1, then the mass-to-charge ratio is equal to the molecular weight of the potential marker represented by the signal. Thus, while some mass spectra plots may show signal intensity as a function of molecular weight, the molecular weight parameter is in fact derived from mass-to-charge ratios.

While many specific embodiments of the invention discussed herein refer to the use of mass-to-charge ratios, it is understood that time-of-flight values, or other values derived from time-of-flight values, may be used in place of mass-to-charge ratio values in any of the specifically discussed exemplary embodiments.

Although each mass spectrum in the analyzed mass spectra can comprise signal strength data as a function of time of flight, the use of mass spectra having signal strength data as a function of mass-to-charge ratio is generally preferred. Time-of-flight values for ions are machine dependent, whereas mass-to-charge ratio values are machine independent. For example, in a time-of-flight mass spectrometry process, the time-of-flight values obtained for ions can depend on the length of the free flight tube in the particular mass spectrometer used. Different mass spectrometers with different free flight tube lengths can produce different time-of-flight values for the same ion. This is not the case for mass-to-charge ratios, since a mass-to-charge ratio is simply the ratio of the mass of an ion to the charge of the ion. Classification models created using mass-to-charge ratio values can also be independent of the particular mass spectrometer used to create them.

The data set may comprise any suitable data and may be entered automatically or manually into a digital computer. The data may be raw or preprocessed before being processed by the classification process run on the digital computer. For example, the raw intensities of signals at predetermined mass-to-charge ratios in the mass spectra may be used as the data set. Alternatively, the raw data may be preprocessed before the classification model is formed. For example, in some embodiments, the log values of the intensities (e.g., base 2) of the signals in the mass spectra may be used to form the data set.

The data set is entered into the digital computer. Computer code that embodies a classification process uses the data set to form a classification model. Exemplary classification processes include hierarchical classification processes such as a classification and regression tree process, multivariate statistical analyses such as a cluster analysis, and non-linear processes such as a neural network analysis. In preferred embodiments, the data set is processed using a classification and regression tree process to produce a classification model such as a classification and regression tree. These and other classification processes and classification models are described in greater detail below.

The created classification model may be predictive or descriptive. For example, the model can be used to predict whether an unknown test biological sample is or is not associated with a particular biological status. Alternatively or additionally, the classification model may be interrogated to identify features in the data that differentiate the biological status(s) being analyzed. A feature includes any aspect of the mass spectra data that can differentiate the particular classes being analyzed. Suitable features that can be identified include, but are not limited to, signal intensities or signal intensity ranges at one or more mass-to-charge ratios, signal shapes (e.g., peak shapes), signal areas (e.g., peak areas), signal widths (e.g., peak widths such as at the bottom of a peak), the number of signals in each mass spectrum, etc. In a typical example, the classification model may indicate that a feature such as a particular signal intensity at a given mass-to-charge ratio differentiates diseased samples from non-diseased samples. In yet another example, the classification model may indicate that a combination of features differentiates diseased samples from non-diseased samples. For example, signal intensity ranges for two or more signals at different mass-to-charge ratios may differentiate a diseased state from a non-diseased state.

In another example, a suitable feature that may be identified as differentiating the different sample classes may be the frequency that signals occur at a particular mass-to-charge ratio within a class. For example, for a diseased class having 100 samples and a normal class having 100 samples, a signal of intensity Y at a mass-to-charge ratio X may be present in the mass spectra of 90 diseased class samples, but may be present in only in 10 samples from the normal class samples. Even though the average intensity of the signals is the same in both the diseased class and the normal class (i.e., an average intensity of Y), the higher number of occurrences of the signal in the cancer patient class indicates that the feature differentiates the diseased class from the normal class. A frequency feature such as this can be identified using the classification model.

Any suitable biological samples may be used in embodiments of the invention. Biological samples include tissue (e.g., from biopsies), blood, serum, plasma, nipple aspirate, urine, tears, saliva, cells, soft and hard tissues, organs, semen, feces, urine, and the like. The biological samples may be obtained from any suitable organism including eukaryotic, prokaryotic, or viral organisms.

The biological samples may include biological molecules including macromolecules such as polypeptides, proteins, nucleic acids, enzymes, DNA, RNA, polynucleotides, oligonucleotides, nucleic acids, carbohydrates, oligosaccharides, polysaccharides; fragments of biological macromolecules set forth above, such as nucleic acid fragments, peptide fragments, and protein fragments; complexes of biological macromolecules set forth above, such as nucleic acid complexes, protein-DNA complexes, receptor-ligand complexes, enzyme-substrate, enzyme inhibitors, peptide complexes, protein complexes, carbohydrate complexes, and polysaccharide complexes; small biological molecules such as amino acids, nucleotides, nucleosides, sugars, steroids, lipids, metal ions, drugs, hormones, amides, amines, carboxylic acids, vitamins and coenzymes, alcohols, aldehydes, ketones, fatty acids, porphyrins, carotenoids, plant growth regulators, phosphate esters and nucleoside diphospho-sugars, synthetic small molecules such as pharmaceutically or therapeutically effective agents, monomers, peptide analogs, steroid analogs, inhibitors, mutagens, carcinogens, antimitotic drugs, antibiotics, ionophores, antimetabolites, amino acid analogs, antibacterial agents, transport inhibitors, surface-active agents (surfactants), mitochondrial and chloroplast function inhibitors, electron donors, carriers and acceptors, synthetic substrates for proteases, substrates for phosphatases, substrates for esterases and lipases and protein modification reagents; and synthetic polymers, oligomers, and copolymers. Any suitable mixture or combination of the substances specifically recited above may also be included in the biological samples.

As noted above, the biological samples from which the data set is created are assigned to a class in a set of two or more classes. Each class is characterized by a different biological status. Preferably, there are only two classes and two biological statuses; one for each of the two classes. For example, one class may have a biological status such as a diseased state while the other biological status may have a status such as a non-diseased state.

As used herein, "biological status" of a sample refers to any characterizing feature of a biological state of the sample or the organism or source from which the sample is derived. The feature can be a biological trait such as a genotypic trait or a phenotypic trait. The feature can be a physiological or disease trait, such as the presence or absence of a particular disease, including infectious disease. The feature also can be a condition (environmental, social, psychological, time-dependent, etc.) to which the sample has been exposed.

Genotypic traits can include the presence or absence of a particular gene or polymorphic form of a gene, or combination of genes. Genetic traits may be manifested as phenotypic traits or exist as susceptibilities to their manifestation, such as a susceptibility to a particular disease (e.g., a propensity for certain types of cancer or heart disease).

Phenotypic traits include, for example, appearance, physiological traits, physical traits, neurological conditions, psychiatric conditions, response traits, e.g., or response or lack of response to a particular drug. Phenotypic traits can include the presence of absence of so-called "normal" or "pathological" traits, including disease traits. Another status is the presence or absence of a particular disease. A status also can be the status of belonging to a particular person or group such as different individuals, different families, different age states, different species, and different tissue types.

In some embodiments, the biological statuses may be, for example, one or more of the following in any suitable combination: a diseased state, a normal status, a pathological status, a drug state, a non-drug state, a drug responder state, a non-drug responder state, and a benign state. A drug state may include a state where patient who has taken a drug, while a non-drug state may include a state where a patient has not taken a drug. A drug responder state is a state of a biological sample in response to the use of a drug. Specific examples of disease states include, e.g., cancer, heart disease, autoimmune disease, viral infection, Alzheimer's disease and diabetes. More specific cancer statuses include, e.g., prostate cancer, bladder cancer, breast cancer, colon cancer, and ovary cancer. Biological statuses may also include beginning states, intermediate states, and terminal states. For example, different biological statuses may include the beginning state, the intermediate state, and the terminal state of a disease such as cancer.

Other statuses may be associated with different environments to which different classes of samples are subjected. Illustrative environments include one or more conditions such as treatment by exposure to heat, electromagnetic radiation, exercise, diet, geographic location, etc. For example, a class of biological samples (e.g., all blood samples) may be from a group of patients who have been exposed to radiation and another class of biological samples may be from a group of patients who have not been exposed to radiation. The radiation source may be an intended radiation source such as an x-ray machine or may be an unintended radiation source such as a cellular phone. In another example, one group of persons may have been on a particular diet of food, while another group may have been on a different diet.

In other embodiments of the invention, the different biological statuses may correspond to samples that are associated with respectively different drugs or drug types. In an illustrative example, mass spectra of samples from persons who were treated with a drug of known effect are created. The mass spectra associated with the drug of known effect may represent drugs of the same type as the drug of known effect. For instance, the mass spectra associated with drugs of known effect may represent drugs with the same or similar characteristics, structure, or the same basic effect as the drug of known effect. Many different analgesic compounds, for example, may all provide pain relief to a person. The drug of known effect and drugs of the same or similar type might all regulate the same biochemical pathway in a person to produce the same effect on a person. Characteristics of the biological pathway (e.g., up- or down-regulated proteins) may be reflected in the mass spectra.

A classification model can be created using the mass spectra associated with the drug of known effect and mass spectra associated with different drugs, different drug types, or no drug at all. Once the classification model is created, a mass spectrum can then be created for a candidate sample associated with a candidate drug of unknown effect. Using the classification model, the mass spectrum associated with the candidate sample is classified. The classification model can determine if the candidate sample is associated with the drug of known effect or another drug of a different type. If, for example, the classification model classifies the candidate sample as being associated with the drug of known effect, then the candidate drug is likely to have the same effect on a person as the drug of known effect. Accordingly, embodiments of the invention can be used, among other things, to discover and/or characterize drugs.

I. Obtaining Mass Spectra

The mass spectra may be obtained by any suitable process. For example, the mass spectra may be retrieved (e.g., downloaded) from a local or remote server computer having access to one or more databases of mass spectra. The databases may contain libraries of mass spectra of different biological samples associated with different biological statuses. Alternatively, the mass spectra may be generated from the biological samples. Regardless of how they are obtained, the mass spectra and the samples used to create the classification model are preferably processed under similar conditions to ensure that any changes in the spectra are due to the samples themselves, and not differences in processing. The mass spectra might be created specifically with a particular classification process in mind, or might be created without reference to a particular classification process used on the data.

In embodiments of the invention, a gas phase ion spectrometer mass may be used to create mass spectra. A "gas phase ion spectrometer" refers to an apparatus that measures a parameter that can be translated into mass-to-charge ratios of ions formed when a sample is ionized into the gas phase. This includes, e.g., mass spectrometers, ion mobility spectrometers, or total ion current measuring devices.

The mass spectrometer may use any suitable ionization technique. The ionization techniques may include for example, an electron ionization, fast atom/ion bombardment, matrix-assisted laser desorption/ionization (MALDI), surface enhanced laser desorption/ionization (SELDI), or electrospray ionization.

In some embodiments, an ion mobility spectrometer can be used to detect and characterize a marker. The principle of ion mobility spectrometry is based on the different mobility of ions. Specifically, ions of a sample produced by ionization move at different rates due to their difference in, e.g., mass, charge, or shape, through a tube under the influence of an electric field. The ions (typically in the form of a current) are registered at a detector and the output of the detector can then be used to identify a marker or other substances in the sample. One advantage of ion mobility spectrometry is that it can be performed at atmospheric pressure.

In preferred embodiments, a laser desorption time-of-flight mass spectrometer is used to create the mass spectra. Laser desorption spectrometry is especially suitable for analyzing high molecular weight substances such as proteins. For example, the practical mass range for a MALDI or a surface enhanced laser desorption/ionization process can be up to 300,000 daltons or more. Moreover, laser desorption processes can be used to analyze complex mixtures and have high sensitivity. In addition, the likelihood of protein fragmentation is lower in a laser desorption process such as a MALDI or a surface enhanced laser desorption/ionization process than in many other mass spectrometry processes. Thus, laser desorption processes can be used to accurately characterize and quantify high molecular weight substances such as proteins.

In a typical process for creating a mass spectrum, a probe with a marker is introduced into an inlet system of the mass spectrometer. The marker is then ionized. After the marker ions are generated, the generated ions are collected by an ion optic assembly, and then a mass analyzer disperses and analyzes the passing ions. The ions exiting the mass analyzer are detected by a detector. In a time-of-flight mass analyzer, ions are accelerated through a short high voltage field and drift into a high vacuum chamber. At the far end of the high vacuum chamber, the accelerated ions strike a sensitive detector surface at different times. Since the time-of-flight of the ions is a function of the mass-to-charge ratio of the ions, the elapsed time between ionization and impact can be used to identify the presence or absence of molecules of specific mass-to-charge ratio.

Figure 2:
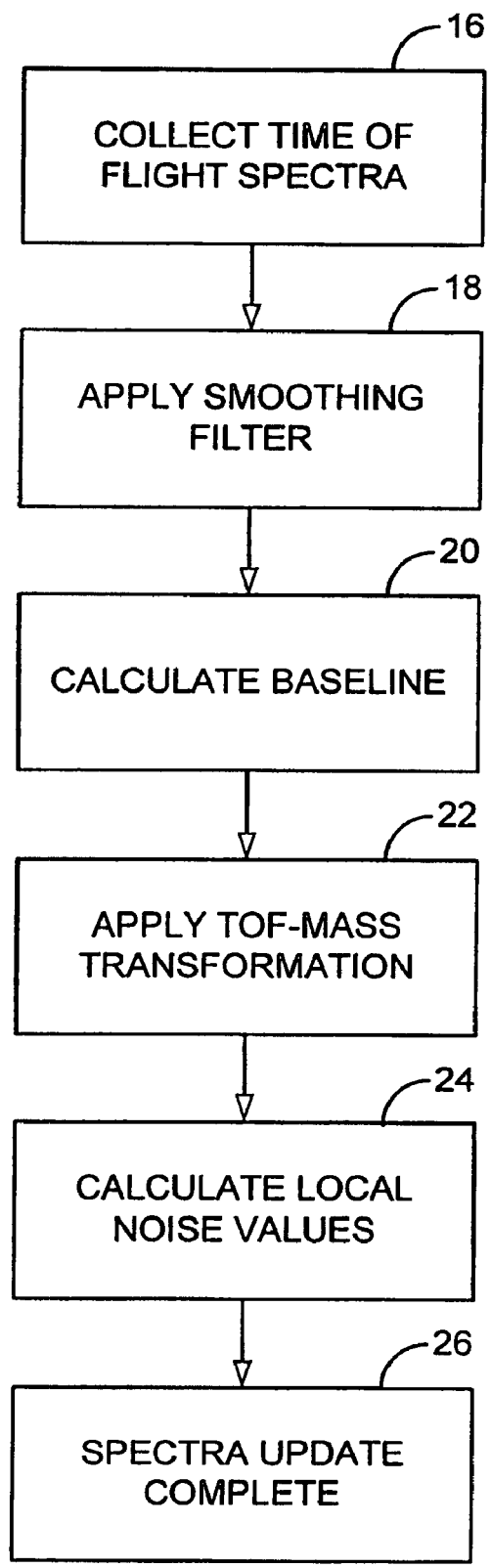
FIG. 2 illustrates a flowchart of a method for creating mass spectra according to an embodiment of the invention.

The time of flight data may then be converted into mass-to-charge ratios to generate a spectrum showing the signal strength of the markers as a function of mass-to-charge ratio. FIG. 2 shows a flowchart illustrating an exemplary method for converting mass spectra based on time-of-flight data into mass-to-charge ratio data. First, time of flight spectra are collected (step 16). Then, a smoothing filter is applied to the time of flight spectra (step 18). Typically, a significant amount of high frequency noise is present in the initially generated spectra. Various filters are applied to reduce noise without corrupting the underlying signal. Then, a baseline is calculated (step 20). This removes a characteristic upward shift that can be characteristic of, for example, a MALDI or a surface enhanced laser desorption/ionization process.

"Surface enhanced" desorption/ionization processes refer to those processes in which the substrate on which the sample is presented to the energy source plays an active role in the desorption/ionization process. In these methods, the substrate, such as a probe, is not merely a passive stage for sample presentation. Several types of surface enhanced substrates can be employed in a surface enhanced desorption/ionization process. In one example, the surface comprises an affinity material, such as anion exchange groups or hydrophilic groups (e.g., silicon oxide), that preferentially bind certain classes of molecules. Examples of such affinity materials include, for example, silanol (hydrophilic), C8 or C16 alkyl (hydrophobic), immobilized metal chelate (coordinate covalent), anion or cation exchangers (ionic) or antibodies (biospecific). The sample is exposed to a substrate bound adsorbent so as to bind analyte molecules according to the particular basis of attraction. Typically non-binding molecules are washed off. When the analytes are biomolecules, an energy absorbing material, e.g., matrix, is typically associated with the bound sample. Then a laser is used to desorb and ionize the analytes, which are detected with a detector.

In another version, the substrate surface comprises a bound layer of energy absorbing molecules, obviating the need to mix the sample with a matrix material, as in MALDI. Surface enhanced desorption/ionization methods are described in, e.g., U.S. Pat. No. 5,719,060 (Hutchens and Yip) and WO 98/59360 (Hutchens and Yip) (U.S. Pat. No. 6,255,047). When a laser desorbs a matrix including an energy absorbing material, some of the matrix material can also be desorbed along with the sample material being analyzed. The baseline calculation adjusts the spectra to take into account the presence of the signal due to desorbed matrix material. Once a baseline is calculated, a time of flight/mass transformation takes place (step 22). In this step, the time of flight data is converted into mass-to-charge ratios. Local noise values are then calculated (step 24). At low mass-to-charge ratios, a significant amount of noise is generated due to the desorbed matrix material. In an ionization desorption process, desorption of the matrix material is less likely at higher mass-to-charge ratios than at lower mass-to-charge ratios. Noise is therefore more likely at lower mass-to-charge ratios than at higher mass-to-charge ratios. Adjustments to the spectra can be made to correct for this effect. After these corrections are made, the spectra update is complete (step 26). By processing mass spectra according to the method shown in FIG. 2, the signal-to-noise ratio of the mass spectrum is improved, allowing better quantitation and comparison of potential markers.

Mass spectra data generated by the desorption and detection of markers can be preprocessed using a digital computer after or before generating a mass spectra plot. Data analysis can include the steps of determining the signal strength (e.g., height of signals) of a detected marker and removing "outliers" (data deviating from a predetermined statistical distribution). For example, the observed signals can be normalized. Normalization is a process whereby the height of each signal relative to some reference is calculated. For example, a reference can be background noise generated by instrument and chemicals (e.g., an energy absorbing molecule) which is set as zero in the scale. Then, the signal strength detected for each marker or other substances can be displayed in the form of relative intensities in the scale desired (e.g., 100). Alternatively, a standard may be admitted with the sample so that a signal from the standard can be used as a reference to calculate relative intensities of the signals observed for each marker or other markers detected.

The digital computer can transform the resulting data into various formats for display. In one format, referred to as "spectrum view or retentate map," a standard spectral view can be displayed. The spectral view depicts the quantity of marker reaching the detector at each particular molecular weight. In another format, referred to as "peak map," only the peak height and mass information are retained from the spectrum view, yielding a cleaner image and enabling signals representing markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as a "difference map view," two or more spectra can be compared, conveniently highlighting signals representing markers and signals representing markers that are up- or down-regulated between samples. Marker profiles (spectra) from any two samples may be compared visually on one plot. Data that can be used to form the data set may be obtained from these and other mass spectra display formats.

II. Forming the Data Set

Once the mass spectra are obtained, a data set such as a known data set is formed. The data set comprises data that is obtained from the mass spectra of the class set of biological samples. The mass spectra data forming the data set can be raw, unprocessed data. For example, raw signal intensity values at identified mass values from the mass spectra may be used to form the data set. In another example, raw signal patterns from mass spectra may be used to form the data set.

In alternative embodiments, data may be preprocessed before it is used to form the classification model. The mass spectra may then be processed in any suitable manner before being used to form the classification model. For example, the signals in the mass spectra may be processed by taking the log values of the signal intensities, removing outliers, removing signals which are less likely to be associated with potential markers, removing signals which have low intensities, etc.

In some embodiments, the data set may comprise raw or preprocessed pattern data that relates to the particular pattern of each mass spectrum. For example, for a mass spectrum comprising many signal peaks, the pattern of the signal peaks may constitute a fingerprint for the biological sample used to create the mass spectrum. The classification process can classify the different spectra according to patterns or pattern segments that may be common to the spectra in the respectively different classes differentiated by the classification model. A computer program such as a neural network program, for example, can receive plural mass spectra of known samples associated with known biological statuses. The neural network can be trained with the mass spectra data so that it can differentiate between mass spectra patterns belonging to the respectively different classes. The trained neural network can then be used to classify a mass spectrum associated with an unknown sample based on the pattern in the mass spectrum.

In other embodiments, the data set comprises data relating to the intensities of the signals in the mass spectra. In these embodiments, some or all of the signals in each mass spectrum may be used to form the data set. For example, the intensities of less than all of the signals (e.g., peaks) in a spectra view type mass spectrum can be used to form the data set. In preferred embodiments, mass-to-charge ratios are identified, and the identified mass-to-charge ratios are used to select signals from the mass spectra. The intensities of these selected signals can be used to form the data set. By using data from less than all signals in each mass spectrum to form the data set, the number of data points that will be processed is reduced so that data processing occurs more rapidly. Data of signals that have a low likelihood of representing acceptable markers may be excluded from the data set.

Mass-to-charge ratios may be identified in any number of ways. For example, the mass-to-charge ratios may be identified by comparing the mass spectra of different classes having different biological statuses. The mass-to-charge ratios of signals that are likely to differentiate the classes may be selected. The comparison may be performed manually (e.g., by a visual comparison) or may be done automatically with a digital computer. For example, mass spectra associated with different classes of samples can be visually compared with each other to determine if the intensity of a signal at a mass-to-charge ratio in a mass spectrum from one sample class is significantly greater than or less than a signal at the same mass-to-charge ratio in a mass spectrum from a different sample class, thus indicating potential differential expression. Mass-to-charge ratios where these signal differences occur may be selected.

Figure 3:
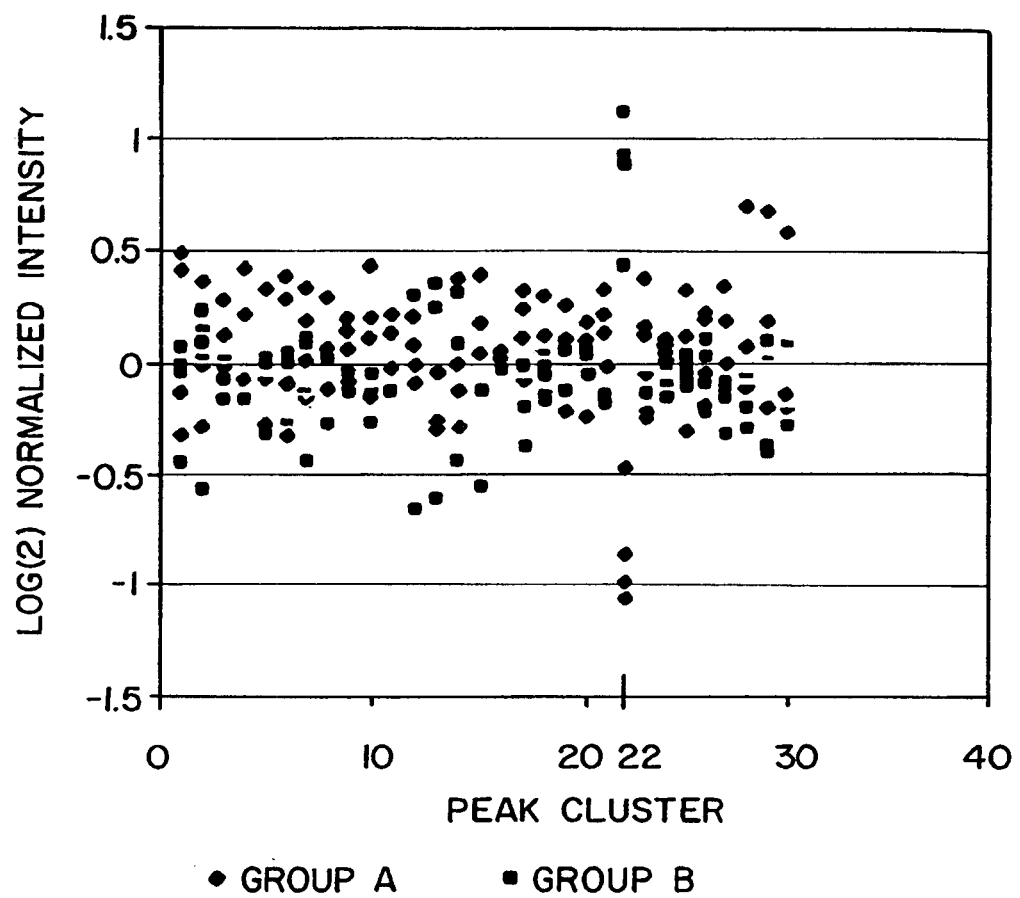
FIG. 3 shows a graph of log normalized intensity as a function of identified peak clusters. The signal intensities from mass spectra from two different groups of samples are shown in the graph.

FIG. 3, for example, shows a graph of log (2) normalized intensity vs. the identified peak clusters. This plot displays the log base 2 normalized intensity values. Each intensity value in a peak cluster has the average intensity value subtracted so a value of zero represents no change from the average. Each unit on the y-axis represents a two-fold difference from the cluster average. Significantly up and down regulated proteins can be identified using a plot such as the one shown in FIG. 3. FIG. 3 shows a graph of log normalized intensity as a function of different signal clusters. The signal intensities from mass spectra from two different groups of samples are shown in the graph. For example, the peak cluster 22 (on the x-axis) in FIG. 3 shows a wide variation between the data points from Group A and Group B. This indicates that the mass-to-charge ratio associated with peak cluster 22 can be identified as a candidate marker location.

Alternatively or additionally, certain predefined criteria may be provided to first select certain signals or signal clusters. The selected signal clusters may then be used to identify particular mass-to-charge ratios. For example, signals or signal clusters having a signal intensity or average signal intensity above or below a certain signal intensity threshold may be automatically selected. Mass-to-charge ratios associated with these selected signals or signal clusters may then be identified.

Figure 4:
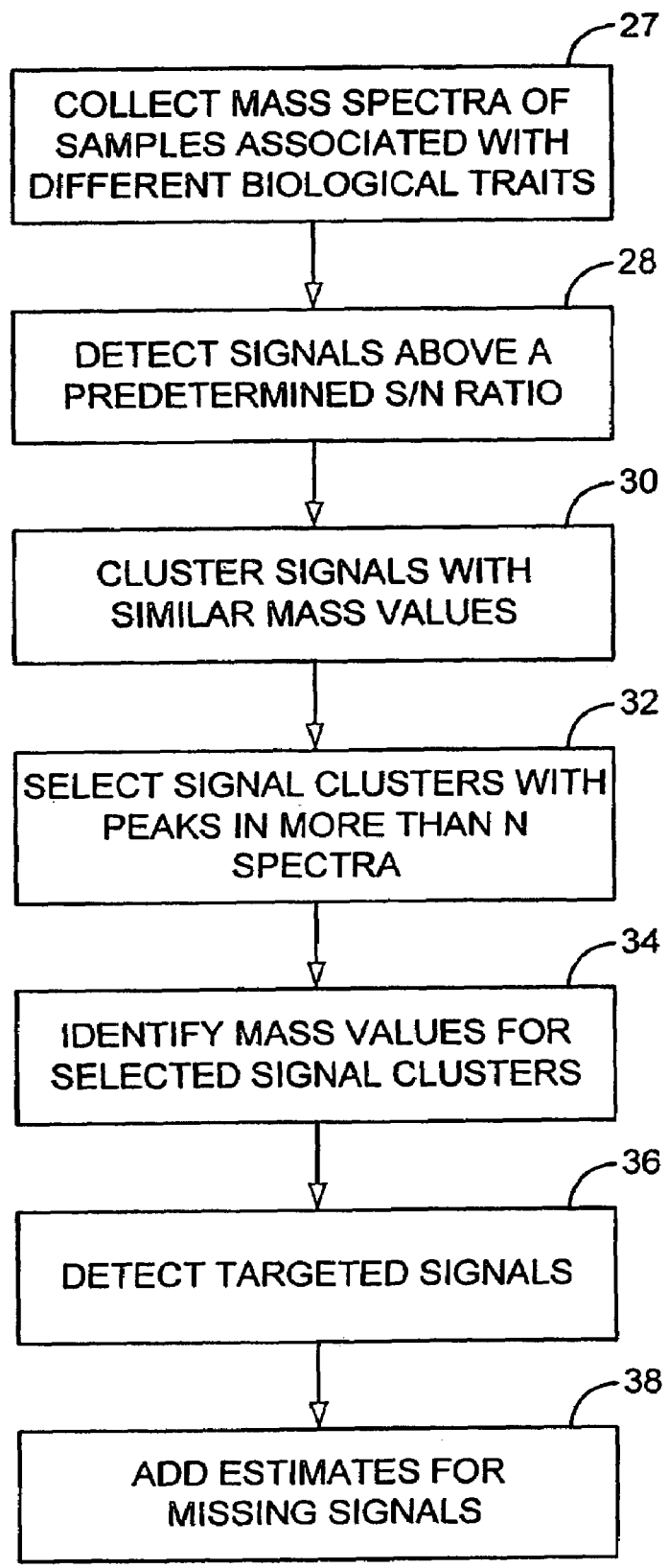
FIG. 4 shows a flowchart illustrating some preferred mass spectra preprocessing procedures according to an embodiment of the invention.

Preferred methods including collecting mass spectra data, preprocessing the data, and processing the preprocessed mass spectral data to form a classification model can be described with reference to FIGS. 4 and 5. With reference to FIG. 4, mass spectra of samples associated with different biological statuses are collected (step 27). The number of samples collected is preferably large. For example, in embodiments of the invention, the number of collected samples may be from about 100 to about 1000 (or more or less than these values). Preferably, all samples used to create the spectra are created under similar conditions so that differences between the samples are reflected in the spectra.

Signals corresponding to the presence of a potential marker are identified in each spectrum. Each such signal is assigned a mass value. Signals above a predetermined signal-to-noise ratio in each mass spectrum in the first group of mass spectra are then detected (step 28). In a typical example, signals with a signal-to-noise ratio greater than a value S may be detected. The value S may be an absolute or a relative value. Then, signals at the mass-to-charge ratios in the mass spectra are clustered together (step 30). Signal clusters that meet predetermined criteria are then selected. For example, in one embodiment, signal clusters having a predetermined number of signals can be selected (step 32). Clusters having less than the predetermined number are discarded. In a typical example, if the number of signals in a cluster is less than 50% of the number of mass spectra, then the signal cluster can be discarded. In some embodiments, the selection process results in anywhere from as few as about 20 to more than about 200 selected signal clusters. Once the signal clusters are selected, the mass-to-charge ratios for these signal clusters can be identified (step 34).

Once the mass-to-charge ratios are identified, "missing signals" for the mass-to-charge ratios can be determined. Some of the mass spectra may not exhibit a signal at the identified mass-to-charge ratios. This group of mass spectra or the samples associated with the mass spectra can be re-analyzed to determine if signals do in fact exist at the identified mass-to-charge ratios (step 36). Estimates are added for any missing signals (step 38). For spectra where no signal is found in a cluster, an intensity value is estimated from the trace height or noise value. The estimated intensity value may be user selectable.

Figure 5:
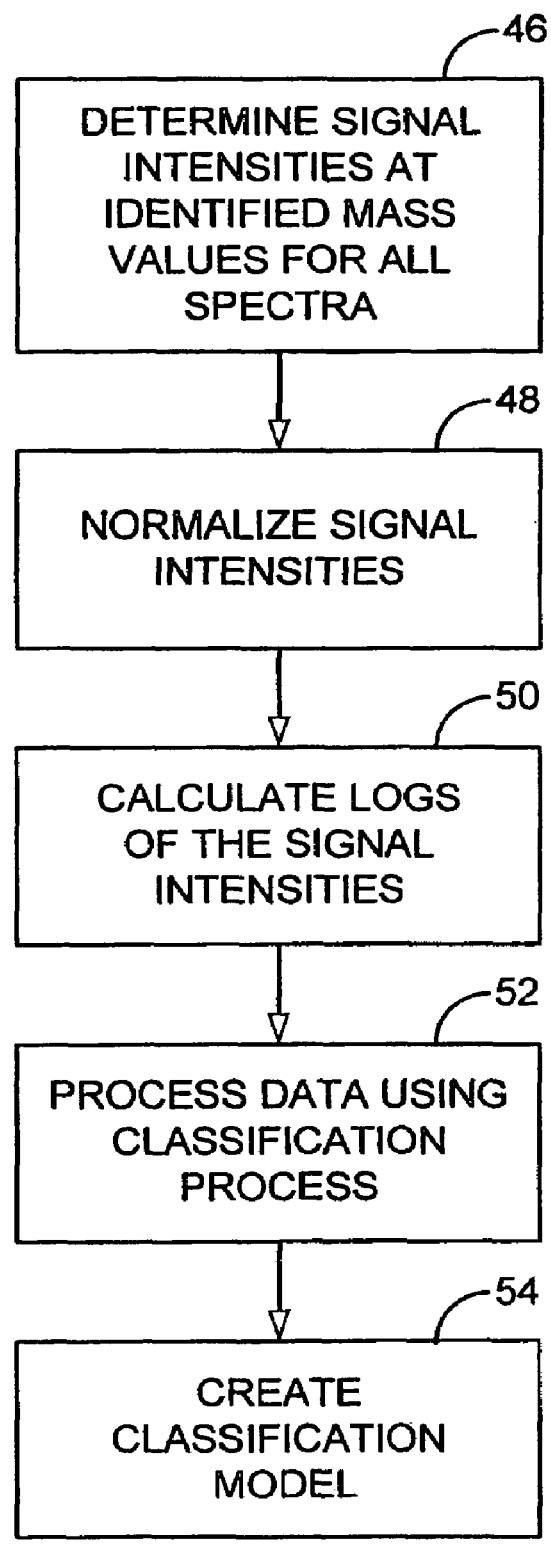
FIG. 5 shows a flowchart illustrating some preferred mass spectra preprocessing procedures and classification model formation procedures according to an embodiment of the invention.

With reference to FIG. 5, once mass-to-charge ratios are identified, intensity values are determined for each signal at the identified mass values for all mass spectra (step 46). The intensity value for each of the signals is normalized from 0 to 100 to remove the effects of absolute magnitude (step 48). Then, the logarithm (e.g., base 2) is taken for each normalized signal intensity (step 50). Taking the logarithm of the signal intensities removes skew from the measurements.

The log normalized data set is then processed by a classification process (step 52) that is embodied by code that is executed by a digital computer. After the code is executed by the digital computer, the classification model is formed (step 54). Additional details about the formation of the classification model are provided below.

III. Forming the Classification Model

A classification process embodied by code that is executed by a digital computer can process the data set. The code can be executed by the digital computer to create a classification model. The code may be stored on any suitable computer readable media. Examples of computer readable media include magnetic, electronic, or optical disks, tapes, sticks, chips, etc. The code may also be written in any suitable computer programming language including, C, C++, etc.

The digital computer may be a micro, mini or large frame computer using any standard or specialized operating system such as a Windows™ based operating system. In other embodiments, the digitial computer may simply be a one or more microprocessors The digital computer may be physically separate from the mass spectrometer used to create the mass spectra. Alternatively, the digital computer may be coupled to or physically incorporated into the mass spectrometer. Mass spectra data can be transmitted from the mass spectrometer to the digital computer manually or automatically. For example, in one embodiment, a known data set may first be obtained from a plurality of mass spectra. The known data set may then be manually entered into a digital computer running code that embodies a classification process. In another embodiment, the generation and/or collection of mass spectra data, the preprocessing of the data, and the processing of the preprocessed data by a classification process may be performed using the same physical computational apparatus.

In some embodiments, the known data set can be characterized as a training set which can "train" a precursor to the classification model or a previously formed classification model. The classification model may be trained and learn as it is formed. For example, in a neural network, the known data set can be used to train the neural network to recognize differences between the classes of data that are entered into the neural network. After an initial classification model is formed, a larger number of samples can be used to further train and refine the classification model so that it can more accurately discriminate between the classes used to form the classification model.

In embodiments of the invention, additional data may be used to form the classification model. The additional data may or may not relate to mass spectra. For instance, in some embodiments, pre-existing marker data may be used in addition to a known data set to form the classification model. For example, mass spectra for a class of prostate cancer patient samples and a class of non-prostate cancer patient samples may be obtained. A known data set may be formed using the mass spectra. A classification model may be formed using the known data set and pre-existing marker data such as pre-existing PSA diagnostic data (e.g., PSA clinical assay data). The additional pre-existing PSA diagnostic data can be used to help differentiate the mass spectra to form the classification model. For example, each mass spectrum may be evaluated to see if a signal at the mass-to-charge ratio corresponding to PSA is more closely associated with a signal intensity characteristic of prostate cancer or a signal intensity characteristic of non-prostate cancer. This information can be used to help assign the mass spectrum and its corresponding sample to a prostate cancer or a non-prostate cancer class. In other embodiments, non-mass spectra data such as the sex, age, etc. of the persons from which the biological samples were taken may also be used to form a classification model. For example, if men are more likely to have a particular disease than women, then this information can also be used to help classify samples and form a classification model.

Any suitable classification process may be used in embodiments of the invention. For example, the classification process may be a hierarchical classification process such as a classification and regression tree process or a multivariate statistical analysis. A multivariate statistical analysis looks at patterns of relationships between several variables simultaneously. Examples of multivariate statistical analyses include well known processes such as discriminate function analysis and cluster analysis. Discriminant function analysis is a statistical method of assigning observations to groups based on previous observations from each group. Cluster analysis is a method of analysis that represents multivariate variation in data as a series of sets. In biology, for example, the sets are often constructed in a hierarchical manner and shown in the form of a tree-like diagram called a dendrogram. Some types of cluster analyses and other classification processes are described in the article by Jain et al., "Statistical Pattern Recognition: A Review", *IEEE Transactions on Pattern Analysis and Machine Intelligence*, Vol. 22, No. 1, January 2000. This article is incorporated herein by reference in its entirety.

Alternatively, the classification process may use a non-linear classification process such as an artificial neural network analysis. An artificial neural network analysis can be trained using the known data set. In general, an artificial neural network can predict the value of an output variable based on input from several other input variables that can impact it. The prediction is made by selecting from a set of known patterns the one that appears most relevant in a particular situation. An artificial neural network conceptually has several neuron elements (units) and connections between them. These units are categorized into three different layers or groups according to their functions. A first group forms an input layer that receives the data entered into the system. A second group forms an output layer that delivers the output data representing an output pattern. A third group comprises a number of intermediate layers, also known as hidden layers that convert the input pattern into an output.

Illustratively, a neural network can be trained to differentiate between laser desorption mass spectra associated with a diseased state and a non-diseased state. Then, a mass spectrum of a test biological sample can be created by a laser desorption process and data relating to this mass spectrum can be input into the trained neural network. The trained neural network can determine if the test biological sample is associated with the diseased state or non-diseased state.

In embodiments of the invention, the classification process preferably includes a hierarchical, recursive partitioning process such as a classification and regression tree process. In embodiments of the invention, the classification and regression tree process is embodied by computer code that can be executed by a digital computer. An exemplary classification and regression tree program is CART 4.0 commercially available from Salford Systems, Inc. (www.salford-systems.com).

One specific classification and regression tree process is a binary recursive partitioning process. The process is binary because parent nodes are always split into exactly two child nodes and recursive because the process can be repeated by treating each child node as a parent. To partition a known data set, questions are asked of the known data set. In embodiments of the invention, the data being partitioned are the mass spectra corresponding to the class set of biological samples. Each mass spectrum can be considered an "instance" to be classified. An exemplary question that may be used to partition the instances may be "Is the signal intensity of the signal at the mass-to-charge ratio X greater than Y?" Each question subdivides the known data set into two groups of more homogeneous composition. Once a best split is found, the classification and regression tree process repeats the search process for each child node, continuing recursively until further splitting is impossible or stopped. Splitting is impossible if only one case remains in a particular node or if all the cases in that node are of the same type.

The questions asked of the data set may be determined by a user or may be automatically determined by a digital computer. In some embodiments, the questions can be arbitrarily generated by a digital computer and the quality of the data splitting determines if the question is acceptable. For example, a question may be asked of the data. If the partitioning results in a statistically significant split of the instances, the question may be kept and used to form the classification and regression tree. The classification and regression tree process identifies the optimal number of questions required to classify the data, compensating for the effects of random error in each sample observation.

The classification and regression tree process looks at all possible splits for all predictor variables included in the analysis. For example, for a data set with 215 instances and 19 predictor variables, the process considers up to 215 times 19 splits for a total of 4085 possible splits. Typically, all such splits are considered when forming a classification and regression tree. Consequently, the formed classification and regression tree process takes into account many different predictor variables in forming the classification model. For example, in a typical embodiment, data of signals at over 100 mass-to-charge ratios in all mass spectra for the class set are taken into account when forming the classification model. In comparison, the differential expression analysis described above takes only one predictor variable into account. Consequently, the classification and regression tree embodiments can provide more accurate classification accuracy than other classification methods since more data from each mass spectrum is used to form the classification model.

To check the accuracy of the model, the classification and regression tree process may employ a computer-intensive technique called cross validation. In a typical cross-validation process, a large tree is grown and is then pruned back. The data set is divided into 10 roughly equal parts, each containing a similar distribution for the biological statuses being analyzed. The first 9 parts of the data are used to construct the largest possible tree. The remaining 1 part of data is used to obtain initial estimates of the error rate of selected sub-trees. The same process is then repeated (growing the largest possible tree) on another 9/10 of the data while using a different 1/10 part as the test sample. The process continues until each part of the data has been held in reserve one time as a test sample. The results of the 10 mini-test samples are then combined to form error rates for trees of each possible size. These error rates are applied to the tree based on the entire data set. Cross validation provides fairly reliable estimates of the independent predictive accuracy of the tree. Even if an independent test sample is not available, a prediction can be made as to how accurately the tree can classify completely fresh data (e.g., data from a plurality of unknown samples).

The classification and regression tree that is created provides a representation of which of the predictor variables (if any) are responsible for the differences between sample groups. The classification and regression tree can be used for classification (predicting what group a case belongs to) and also be used for regression (predicting a specific value). It can also be used to identify features that may be important in discriminating between the classes being analyzed. For example, the classification model may indicate that one or more signal intensity values at specific mass-to-charge ratios, alone or in combination, are important features that differentiate the classes being analyzed.

The classification and regression tree graphically displays the relationships found in data. One primary output of the classification and regression tree process is the tree itself. The tree can serve as one aspect of a classification model that can be visually analyzed by a user. Unlike non-linear techniques such as a neural network analysis, the visual presentation provided by the tree makes the classification analysis very easy to understand and assimilate. As a result, users tend to trust the results of decision trees more than they do "black box" classification models such as those characteristic of trained neural networks. This makes the classification and regression tree a desirable classification model for various health care and regulatory personnel (e.g., the Food and Drug Administration), and patients, who may want to have a detailed understanding of the analysis used to create the classification model. The trees can also be used to discover previously unknown connections between the data and the biological statuses being analyzed.

The classification and regression tree process has other advantages over classification processes such as a neural network analysis. For example, classification and regression tree programs are more efficient than neural networks, which typically require a large number of passes of the training set data, sometimes numbering in the thousands. The number of passes required to build a decision tree, however, is no more than the number of levels in the tree. There is no predetermined limit to the number of levels in the tree, although the complexity of the tree as measured by the depth and breadth of the tree generally increases as the number of predictor variables increases.

Also, using the classification and regression tree model, features that may discriminate between the classes may be identified. The identified features in the data may be characteristic of the biological status(es) being analyzed. For example, the classification model may indicate that a combination of features is associated with a particular biological status. For example, the model may indicate that specific signal intensities at different mass-to-charge ratios differentiate a diseased state from a non-diseased state. In comparison to conventional differential analysis processes, in embodiments of the invention, many different variables may be analyzed. The classification model can identify a single predictor variable or can identify multiple predictor variables that may differentiate the biological statuses being analyzed.

IV. Using the Classification Model

The classification model may be used to classify an unknown sample into a biological status. In this method the mass spectrum of a test sample can be compared to the classification model associated with a particular biological status to determine whether the sample can be properly classified with the biological status. A mass spectrum of the unknown biological sample can be obtained, and data obtained from a mass spectrum of the unknown sample can be entered into a digital computer. The entered data may be processed using a classification model. The classification model may then classify the unknown sample into a particular class. The class may have a particular biological status associated with it, and the person can be diagnosed as having that particular biological status.

This method has particular use for clinical applications. For example, in the process of drug discovery, one may wish to determine whether a candidate molecule produces the same physiological result as a particular drug or class of drugs (e.g., the class of seratonin re-uptake inhibitors) in a biological system. A classification model is first developed that discriminates biological systems based on exposure to the drug or class of drugs of interest (e.g., persons or test animals). Then, the biological system is exposed to the test molecule and a mass spectrum of a sample from the system is produced. This spectrum is then classified as belonging or not belonging to the classification of known drug or group of drugs against which it is being tested. If the candidate molecule is assigned to the class, this information is useful in determining whether to perform further research on the drug.

In another application, a classification model is developed that discriminates various toxic and non-toxic biological states. Toxic status can result from, e.g., exposure to a drug or class of drugs. That is, a classification model can be developed that indicates whether or not a drug or class of drugs produces a toxic response in a biological system (e.g., in vivo or in vitro model systems including liver toxicity). Then, a drug that is in development or in clinical trials can be tested on the system to determine whether a spectrum from a sample from the system can be classified as toxic or not. This information also is useful in toxicity studies during drug development.

In another application, a classification model is developed that discriminates between persons who are responders and non-responders to a particular drug. Then, before giving a drug to a person who is not known to be a responder or non-responder, a sample from the person is tested by mass spectrometry and assigned to the class of responders or non-responders to the drug.

In another application, a classification model is developed that distinguishes person having a disease from those who do not have the disease. Then a person undergoing diagnostic testing can submit a sample for classification into the status of having the disease and not having the disease. Thus, this method is useful for clinical diagnostics.

One embodiment is directed to analyzing cancer. Pathologists grade cancers according to their histologic appearance. Features of low-grade cancers include enlarged nuclei with a moderate increase in nuclear/cytoplasmic ratio, small number of mitoses, moderate cytologic heterogeneity, and retention of generally normal architecture. Features of high-grade cancers include enlarged, bizarre looking nuclei with a high nuclear/cytoplasmic ratio; increased number of mitoses, some of which may appear a typical; and little or no resemblance to normal architecture. It is useful to develop a classification model that distinguishes a biological sample coming from un-diseased, low-grade cancer, and high-grade cancer, since this diagnosis often dictates therapeutic decisions as well as can predict prognosis. The sample can be a solid tissue biopsy or a fine needle aspirate of the suspected lesion. However, in another embodiment, the samples can derive from more easily collected sources from the group of individuals being tested, such as urine, blood or another body fluid. This is particularly useful for cancers that secrete cells or proteins into these fluids, such as bladder cancer, prostate cancer and breast cancer. Upon establishment of the classification model for these states, the model can be used to classify a sample from a person subject to diagnostic testing. In another application, a classification model is developed that discriminates between classes of individuals having a particular physical or physiological trait that is not pathologic. Then, individuals unknown to have the trait can be classified by testing a sample from the individual and classifying a spectrum into the class having the trait, or outside the class having the trait.

The classification model can also be used to estimate the likelihood that an unknown sample is accurately classified as belonging to a class characterized by a biological status. For instance, in a classification and regression tree, the likelihood of potential misclassification can be determined. Illustratively, a classification and regression tree model that differentiates a diseased state from a non-diseased state classifies an unknown sample from a patient. The model can estimate the likelihood of misclassification. If, for example, the likelihood of disease misclassification is less than 10%, then the patient can be informed that there is a 90% chance that he has the disease.

V. Systems Including Computer Readable Media

Figure 6:
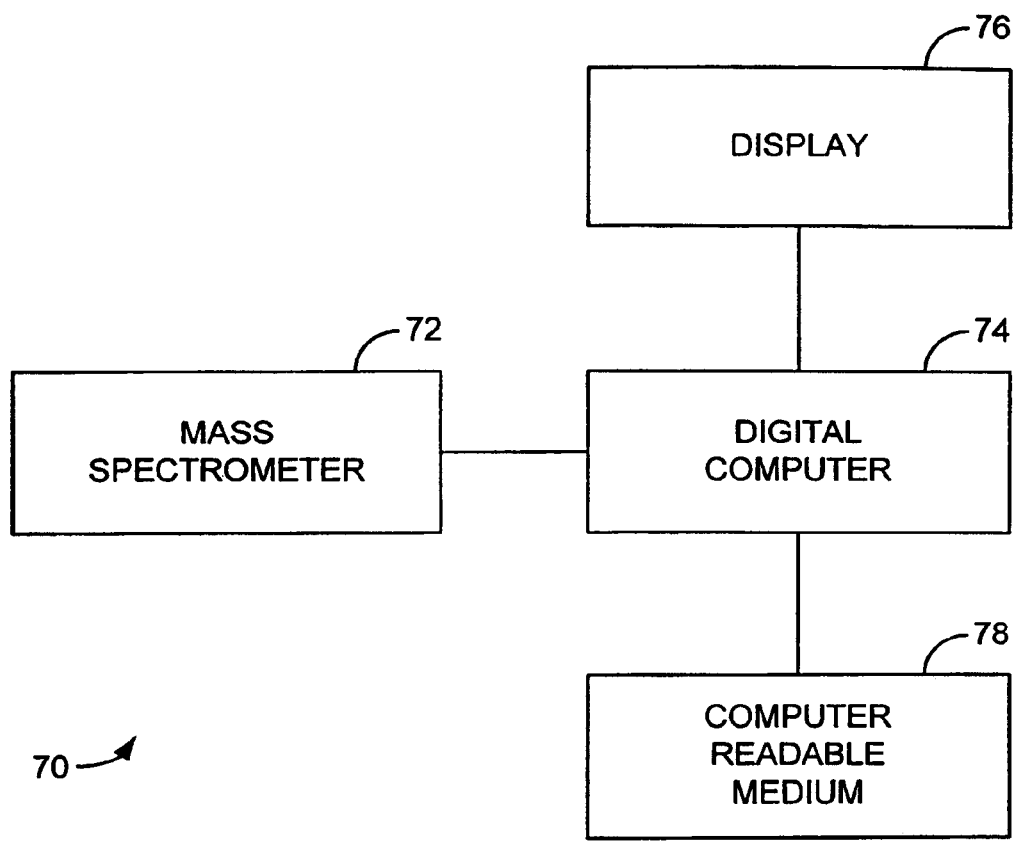
FIG. 6 shows a block diagram of a system according to an embodiment of the invention.

Some embodiments of the invention are directed to systems including a computer readable medium. A block diagram of an exemplary system incorporating a computer readable medium and a digital computer is shown in FIG. 6. The system 70 includes a mass spectrometer 72 coupled to a digital computer 74. A display 76 such as a video display and a computer readable medium 78 may be operationally coupled to the digital computer 74. The display 76 may be used for displaying output produced by the digital computer 74. The computer readable medium 78 may be used for storing instructions to be executed by the digital computer 74.

The mass spectrometer can be operably associated with the digital computer 74 without being physically or electrically coupled to the digital computer 74. For example, data from the mass spectrometer could be obtained (as described above) and then the data may be manually or automatically entered into the digital computer 74 using a human operator. In other embodiments, the mass spectrometer 72 can automatically send data to the digital computer 74 where it can be processed. For example, the mass spectrometer 72 can produce raw data (e.g., time-of-flight data) from one or more biological samples. The data may then be sent to the digital computer 74 where it may be pre-processed or processed. Instructions for processing the data may be obtained from the computer readable medium 78. After the data from the mass spectrometer is processed, an output may be produced and displayed on the display 76.

The computer readable medium 78 may contain any suitable instructions for processing the data from the mass spectrometer 72. For example, the computer readable medium 78 may include computer code for entering data obtained from a mass spectrum of an unknown biological sample into the digital computer 74. The data may then be processed using a classification model. The classification model may estimate the likelihood that the unknown sample is accurately classified into a class characterized by a biological status.

Although the block diagram shows the mass spectrometer 72, digital computer 74, display 76, and computer readable medium 78 in separate blocks, it is understood that one or more of these components may be present in the same or different housings. For example, in some embodiments, the digital computer 74 and the computer readable medium 76 may be present in the same housing, while the mass spectrometer 72 and the display 76 are in different housings. In yet other embodiments, all of the components 72, 74, 76, 78 could be formed into a single unit.

EXAMPLE

A plurality of mass spectra was generated from biological samples from a set of biological samples. The set included a first class of serum from normal patients and a second class of serum from patients with prostate cancer. A serum sample from each patient was run through a surface enhanced laser desorption/ionization system commercially available from Ciphergen Biosystems, Inc. of Fremont, Calif. Ciphergen Biosystem's ProteinChip® technology was also used in this example. Additional details about ProteinChip® technology can be found at the Website www.ciphergen.com. The resulting output for each sample was a mass spectrum plot of signal intensity vs. mass-to-charge ratio. Discrete peaks represented the signals in the mass spectra.

The intensities of the signals at the particular mass-to-charge ratios corresponded to the amount of proteins having the particular mass-to-charge ratios. For example, high signal intensities indicate high concentrations of proteins. Signals in each mass spectrum were located, quantified, and selected. In this example, segments of a mass spectrum were considered acceptable signals if they had intensity values at least twice as great as the surrounding noise level. Signals in the mass spectra at approximately the same mass-to-charge ratios were clustered together in all mass spectra. After clustering, about 250 signal clusters were identified and were labeled P1 through P250. Each signal cluster, P1 through P250, corresponded to a specific mass-to-charge ratio and was characterized as a "predictor variable".

The signal intensities at the identified mass-to-charge ratios for each mass spectrum formed the known data set. These signal intensities were entered into a classification and regression tree program, CART 4.0, commercially available from Salford Systems, Inc. (www.salford-systems.com). The program was executed by a digital computer. The digital computer formed a classification and regression tree. Using the data, each sample was classified as normal or cancer.

After the mass spectra data was input, the digital computer produced a tree such as the one shown in FIG. 6. In this example, class 0 is normal while class 1 is cancer. Each mass spectrum can be characterized as an "instance" which is classified in the tree.

Each box in the tree represents a "node". The top node, Node 1, is called the root node. The decision tree grows from the root node, splitting the data at each level to form new nodes. Branches connect the new nodes. Nodes that do not experience further splitting are called terminal nodes. The terminal nodes in the tree shown in FIG. 6 are labeled Terminal Nodes 1 to 7. As will be explained in further detail below, Terminal Nodes 1 to 7 can be used to classify an unknown sample and can thus be used for prediction.

In each node, the majority sets the classification for the entire node. For example, Terminal Node 1 has four patients. Of these four patients, all four patients have cancer. Terminal Node 1 is therefore characterized as a cancer node. Because all instances have the same value (cancer), this node is characterized as "pure" and will not be split further. If Terminal Node 1 included three cancer patients and one normal patient, the node would still be characterized as a cancer node since a majority of the patients are cancer patients. In this example, the one normal patient would be considered incorrectly classified.

In FIG. 6, each node contains information about the number of instances at that node, and about the distribution of the biological status, cancer. The instances at the root node (Node 1) are all of the instances in the mass spectra data set. Node 1 contains 194 instances, of which 96 are normal and 98 are cancer. Node 1 is splits into two new nodes, Node 2 and Node 5. The data split is determined by determining whether the average signal intensity for the cluster P127 is less than or equal to 3.2946. The average signal intensities, as well as the value 3.2946 were on a relative scale. If the answer to this question is yes, then the corresponding instances are placed in Node 2. If the answer to this question is no, then the corresponding instances are placed in Node 5. In this example, the mass spectra of 85 cancer patients and 11 normal patients had a signal intensity less than or equal to 3.2946 at the mass-to-charge ratio associated with the predictor variable P127 and were placed in Node 2. The mass spectra of 85 normal patients and 13 cancer patients had a signal intensity greater than 3.2946 at the mass-to-charge ratio associated with the predictor variable P127 and were placed in Node 5. Similar partitioning using different splitting rules occurred at the other nodes to form the tree.

The prediction performance of the classification and regression tree can be described with reference to the Tables 1 and 2.

TABLE 1

Misclassification for Learn Data

| Class | N Cases | N Misclassified | Percent Error |
|---|---|---|---|
| 0 (Normal) | 96 | 0 | 0 |
| 1 (Cancer) | 98 | 0 | 0 |

TABLE 2

Misclassification for Test Data

| Class | N Cases | N Misclassified | Percent Error |
|---|---|---|---|
| 0 (Normal) | 96 | 9 | 9.38 |
| 1 (Cancer) | 98 | 11 | 11.22 |

The classification and regression tree program divided the known data set into two groups. About 90% of the data was used as a learning set and about 10% was used as a test set. A classification and regression tree is initially formed using the learning set data. After the tree was formed, it was tested with the remaining 10% test data to see how accurately the classification and regression tree classifies data. With reference to Table 1, all of the learning set data was corrected classified using the formed classification and regression tree. With reference to Table 2, the percent error rates for classifying the normal case and the cancer case test data were 9.38% and 11.22%, respectively. Conversely, the classification success rate was 90.62% and 88.78% for the normal cases and the cancer cases, respectively.

Classification success rates such as these indicate that the classification and regression tree is a highly accurate model for classifying unknown biological samples. In the classification process, multiple predictor variables are considered in the classification scheme. Much more data can be used from a mass spectrum to classify the sample associated with the mass spectrum than the previously described differential analysis procedure, which only uses average signal intensities at a single mass-to-charge ratio to classify a test patient. Accordingly, the classification model can be more accurate in classifying a test patient then many conventional classification models.

Once grown, the tree can be used to classify an unknown sample by starting at the root (top) of the tree and following a path down the branches until a terminal node is encountered. The path is determined by imposing the split rules on the values of the predictor variables in the mass spectrum for the unknown sample. For example, if a mass spectrum of an unknown serum sample from a test patient has signals with intensities of 1.0, 0.05, and 0.9 at the mass-to-charge ratios of predictor variables P127, P193, and P187 respectively, then the test patient would be classified in Node 1, Node 2, Node 3, and then finally Terminal Node 1. Terminal Node 1 is a cancer node and the patient would be classified as being a cancer patient.

Figure 7:
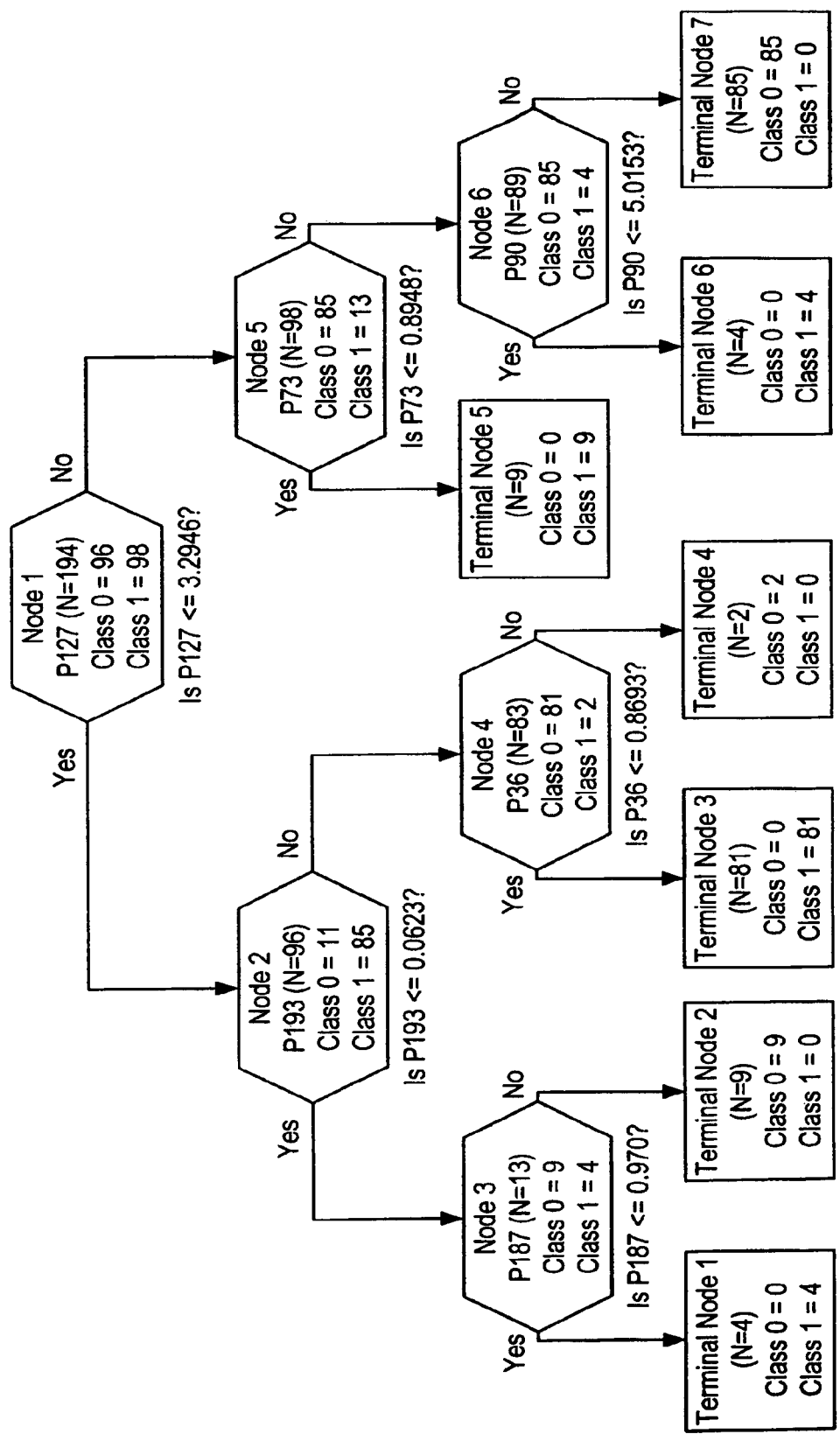
FIG. 7 shows a classification and regression tree according to an embodiment of the invention.

FIG. 7 shows a table of variable importance of each of some of the predictor variables (e.g., signal clusters). The variable importance table ranks the predictor variables by how useful they were in building the classification and regression tree. If a specific predictor variable strongly differentiates the mass spectra data, then it is important in building the classification tree. To calculate a variable importance score, CART looks at the improvement measure attributable to each variable in its role as a surrogate to a primary split. The values of these improvements are summed over each node and totaled, and are scaled relative to the best performing variable. The variable with the highest sum of improvements is scored 100, and all other variables will have a lower score ranging downwards towards zero.

In FIG. 7, the classification model indicates that the predictor variables P36, P127, and P90 are more important than other predictor variables in forming the classification and regression tree. They are consequently more important than other predictor variables in discriminating between the classes, cancer and non-cancer. The mass-to-charge ratios associated with these predictor variables are also associated with potential markers that differentiate prostate cancer samples from non-prostate cancer samples. Accordingly, the classification model can be used to identify one or more markers that may discriminate between classes being analyzed.

Figure 9:
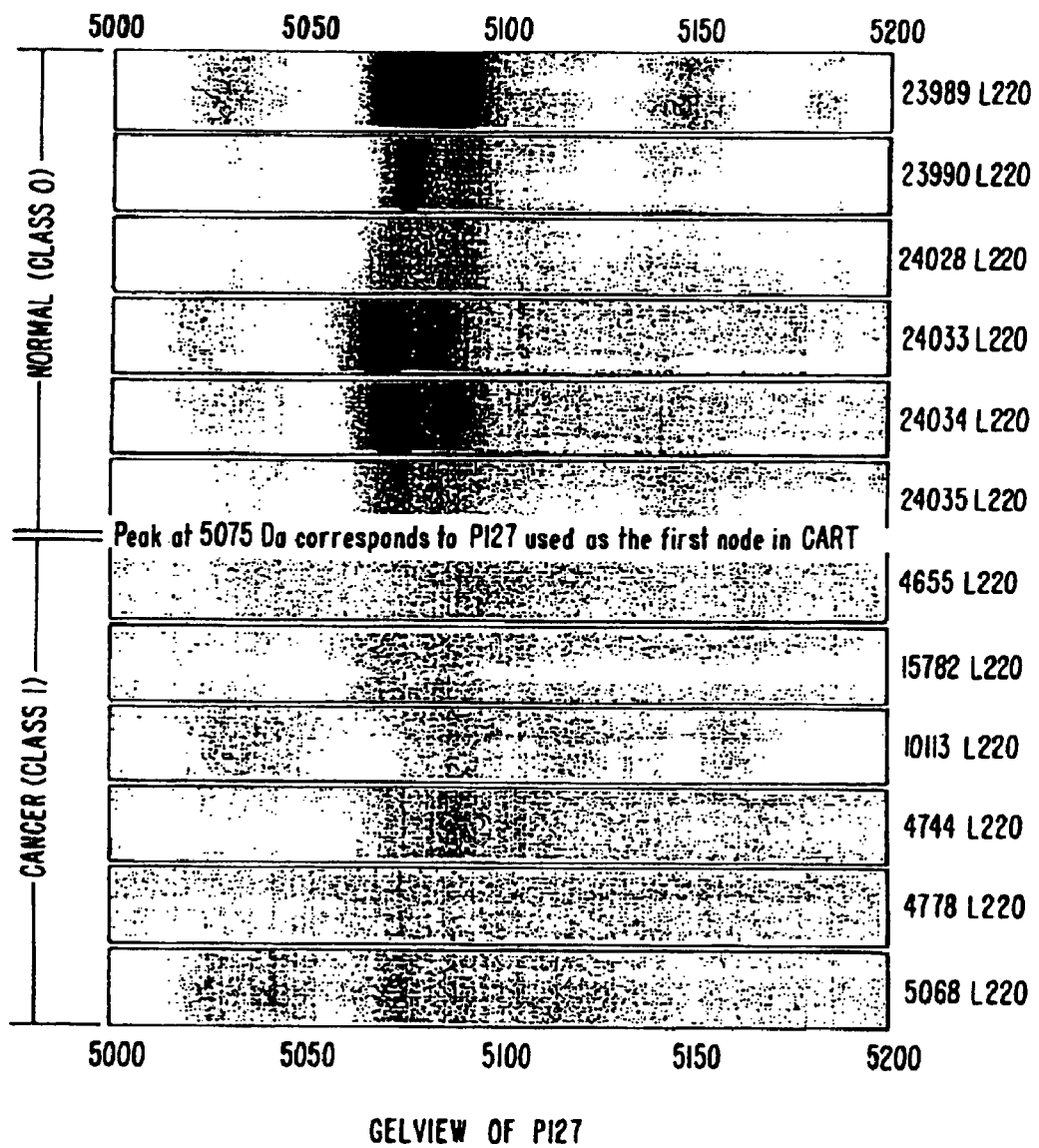
FIG. 9 shows gel views obtained from different samples from cancer patients and normal patients.
Figure 10:
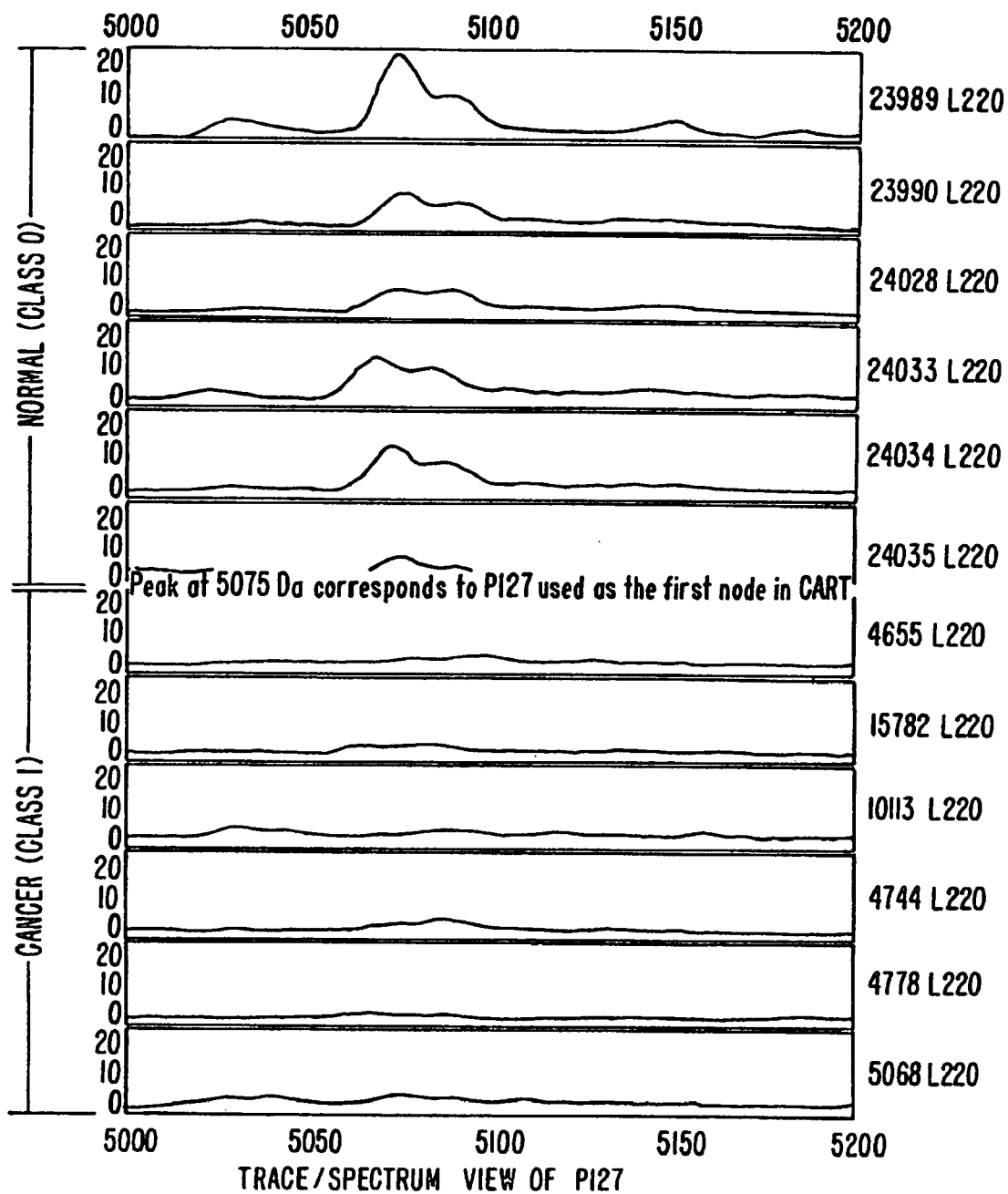
FIG. 10 show spectral views obtained from different samples from cancer and normal patients.

The effectiveness of the tree model can be confirmed with reference to FIGS. 8 and 9. The views in FIG. 8 are gel views while the views in FIG. 9 are trace views. The spectra are zoomed into the signal represented by P127 at a mass-to-charge ratio of 5075 daltons (charge=+1). FIGS. 8 and 9 show that markers in samples from six prostate cancer patients and six non-prostate cancer patients are differentially expressed at the mass value of 5075 daltons corresponding to the predictor variable P127. As shown in the tree in FIG. 6, the predictor variable P127 is the first node in the tree. Also, as shown in FIG. 7, the predictor variable P127 was shown to be more effective in differentiating the prostate cancer class of samples from the non-prostate cancer patient class of samples than most other predictor variables.

While the foregoing is directed to certain preferred embodiments of the present invention, other and further embodiments of the invention may be devised without departing from the basic scope of the invention. Such alternative embodiments are intended to be included within the scope of the present invention. Moreover, the features of one or more embodiments of the invention may be combined with one or more features of other embodiments of the invention without departing from the scope of the invention.

All publications (e.g., Websites) and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A method for analyzing mass spectra, the method comprising:
    detecting signals including signal intensifies in a plurality of spectra, wherein each spectrum in the plurality of spectra comprises data representing signal strength as a function of time-of-flight, mass-to-charge ratio, or a value derived from time-of-flight or mass-to-charge ratio;
    forming at least one signal cluster by clustering signals with similar times-of-flight, mass-to-charge ratios, or values derived from times-of-flights or mass-to-charge ratios;
    determining a predetermined number of signals, wherein the predetermined number of signals represents a minimum number of signals for a selected signal cluster;
    selecting one or more signal clusters from the plurality of signal clusters if the number of signals in a signal cluster meets or exceeds the predetermined number of signals and excluding one or more signal clusters from the plurality of signal clusters if the number of signals in a signal cluster is below the predetermined number of signals; and
    selecting the times-of-flights, the mass-to-charge ratios, or the values derived from the times-of-flights or the mass-to-charge ratios of the selected one or more signal clusters.

2. The method of claim 1 wherein the plurality of mass spectra is a first plurality of mass spectra and wherein the method further comprises:
    forming a second plurality of mass spectra, wherein the second plurality of mass spectra is formed using the selected times-of flights, the mass-to-charge ratios, or the values derived from the selected times-of flights or mass-to-charge ratios.

3. The method of claim 2 further comprising normalizing signal intensity values in the second plurality of mass spectra.

4. The method of claim 2
    wherein the plurality of mass spectra is from a plurality of samples, and wherein each sample is, or is to be assigned to a class within a class set comprising two or more classes, each class being characterized by a different biological status.

5. The method of claim 2 further comprising modifying the second plurality of mass spectra by adding estimates for missing signals.

6. The method of claim 1 wherein the plurality of spectra is generated using a surface enhanced laser desorption ionization process.

7. A computer readable medium comprising:
    code for detecting signals including signal intensities in a plurality of spectra, wherein each spectrum in the plurality of spectra comprises data representing signal strength as a function of time-of-flight, mass-to-charge ratio, or a value derived from time-of-flight or mass-to-charge ratio;
    code for forming at least one signal cluster by clustering signals with similar times-of-flights, mass-to-charge ratios, or values derived from times-of-flights or mass-to-charge ratios;
    code for determining a redetermined number of signals, wherein the predetermined number of signals represents a minimum number of signals for a selected signal cluster;
    code for selecting one or more signal clusters from the plurality of signal clusters of the number of signals in a signal cluster meets or exceeds the predetermined number of signals and excluding one or more signal clusters from the plurality of signal clusters if the number of signals in a signal cluster is below the predetermined number of signals; and
    code for selecting the times-of-flights, the mass-to-charge ratios, or the values derived from the times-of-flights or the mass-to-charge ratios of the selected one or more signal clusters.

8. The computer readable medium of claim 7 wherein the plurality of mass spectra is a first plurality of mass spectra and wherein the computer readable medium further comprises:
    code for forming a second plurality of mass spectra, wherein the second plurality of mass spectra is formed using the times-of-flights, the mass-to-charge ratios, or the values derived from the times-of-flights or mass-to-charge ratios obtained from the selected signal clusters.

9. The computer readable medium of claim 8 further comprising code for normalizing signal intensity values in the second plurality of mass spectra.

10. The computer readable medium of claim 8 further comprising code for modifying the second plurality of mass spectra by adding estimates for missing signals.

11. A system comprising:
a gas phase ion spectrometer;
a digital computer adapted to process data from the gas phase ion spectrometer; and
the computer readable medium of claim 7 in operative association with the digital computer.

12. The computer readable medium of claim 7 wherein the plurality of spectra is generated using a surface enhanced laser desorption ionization process.

* * * * *

UNITED STATES PATENT AND TRADEMARK OFFICE
CERTIFICATE OF CORRECTION

PATENT NO.        : 7,027,933 B2                                    Page 1 of 1
APPLICATION NO.   : 10/669499
DATED             : April 11, 2006
INVENTOR(S)       : Gavin et al.

It is certified that error appears in the above-identified patent and that said Letters Patent is hereby corrected as shown below:

Please correct inventors to read: Item [76]

-- Edward J. Gavin, San Jose, CA;

Leonid Braginsky, Newon, MA;

Cynthia Nakatani, San Jose, CA;--

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,027,933 B2 | Page 1 of 1 |
| APPLICATION NO. | : 10/669499 | |
| DATED | : April 11, 2006 | |
| INVENTOR(S) | : Gavin et al. | |

It is certified that error appears in the above-identified patent and that said Letters Patent is hereby corrected as shown below:

Please correct inventors to read: Item [76]
-- Edward J. Gavin, San Jose, CA;
  Leonid Braginsky, Newton, MA;
  Cynthia Nakatani, San Jose, CA;--

Signed and Sealed this

Twelfth Day of December, 2006

JON W. DUDAS
*Director of the United States Patent and Trademark Office*